United States Patent [19]

Slater et al.

[11] Patent Number: 5,547,976

[45] Date of Patent: Aug. 20, 1996

[54] FURTHER INDOLE DERIVATIVES WITH ANTIVIRAL ACTIVITY

[75] Inventors: Martin J. Slater; George S. Cockerill; Edward Littler; Clive L. Yeates, all of Beckenham, Great Britain

[73] Assignee: Burroughs Wellcome Co., Research Triangle Park, N.C.

[21] Appl. No.: 290,921

[22] PCT Filed: Mar. 19, 1993

[86] PCT No.: PCT/GB93/00571

§ 371 Date: Aug. 23, 1994

§ 102(e) Date: Aug. 23, 1994

[87] PCT Pub. No.: WO93/18766

PCT Pub. Date: Sep. 30, 1993

[30] Foreign Application Priority Data

Mar. 20, 1992 [GB] United Kingdom ............... 9206056
Mar. 27, 1992 [GB] United Kingdom ............... 9206810

[51] Int. Cl.⁶ .................... A61K 31/395; C07D 403/14
[52] U.S. Cl. ............................. 514/410; 548/416
[58] Field of Search ..................... 548/416; 514/410

[56] References Cited

U.S. PATENT DOCUMENTS

| | | | |
|---|---|---|---|
| 4,524,145 | 6/1985 | Matson | 514/43 |
| 4,567,143 | 1/1986 | Matson | 435/119 |

FOREIGN PATENT DOCUMENTS

| | | |
|---|---|---|
| 2015632 | 11/1990 | Canada . |
| 0115350 | 8/1984 | European Pat. Off. . |
| 0175284 | 3/1986 | European Pat. Off. . |
| 0269025 | 6/1988 | European Pat. Off. . |
| 0328000 | 8/1989 | European Pat. Off. . |
| 0370236 | 5/1990 | European Pat. Off. . |
| 0388956 | 9/1990 | European Pat. Off. . |
| 0397147 | 11/1990 | European Pat. Off. . |
| 0410389 | 1/1991 | European Pat. Off. . |
| 0434057 | 6/1991 | European Pat. Off. . |
| 0445736 | 9/1991 | European Pat. Off. . |
| 0450327 | 10/1991 | European Pat. Off. . |
| WO91/09034 | 6/1991 | WIPO . |
| WO91180003 | 11/1991 | WIPO . |

OTHER PUBLICATIONS

Heterocycles, 34(7), 1285–8, (1992) Somei et al.
J. Antibiot, 45(2). 278–9 (1992) Osada et al.
Tetrahedron, 47(37), 7739–50, (1991) Bonjouklian et al.
J. Biol Chem, 266(24), 15771–81, (1991) Toullec et al.
J. Antibiot, 44(7), 723–8, (1991) Kojiri et al.
J. Chem. Soc, Perkins Trans 1,(9) 2475–80, (1990) Hughes et al.
J. Antibiot, 42(12), 1784–1789, Golik et al, (1989).
J. Antibiot, 43(1), 125–7, (1990) Kaneko et al.
J. Org. Chem, 54(4), 824–8, (1989) Bergman et al.
Arch Pharm (Weinheim, Ger), 325(6), 353–6, (1992) Pindur et al.
J. Antibiot, 39(8), 1066–71, (1986) Nakanishi et al.
J. Antibiot, 39 (8), 1071–8, (1986) Yasuzawa et al.
J. Antibiot, 42 (110), 1547–55, (1989) Matson et al.
Tetrahedron Letts, 26 (34) 4015–8, (1985) Kaneko et al.
Tetrahedron Letts, 26 (34), 4011–14, (1985) Nettleton et al.
Tetrahedron, 40 (14), 2795–7, (1984) Magnus et al.
Biochemistry, 31 (48), 12069–75, (1992) Yamashita et al.
J. Ind. Microbiol, 6 (4), 291–4, (1990) Lam et al.
Novel Microb Prod. Med. Agric. (Pap. Int. Conf. Biotechnol Microb Prod.), 1st Meeting date 1988, 63–6. Edited Demain. Elsevier: Amsterdam, (1989) Lam et al.
J. Ind. Microbiol, 4(2), 105–8, (1989) Lam et all.
J. Nat. Prod, 51(5), 937–40, (1988) Pearce et al.
In Vivo, 1 (1), 47–52, (1987) Rose et al.
J. Org. Chem, 52 (7), 1177–85, (1987) Joyce et al.
Tetrahedron Letts, 24 (13), 1441–4, (1983) Hughes et al.
Tetrahedron Letts, 28 (38), 4441–4, (1987) Bergman et al.
Heterocycles, 21 (1), 309–24, (1984) Weinreb et al.
J. Org. Chem, 57(7), 2105–14, (1992) Moody et al.
J. Antibiot, 43(2), 163–7, (1990) Osada et al.

*Primary Examiner*—Joseph K. McKane
*Attorney, Agent, or Firm*—Nixon & Vanderhye

[57] ABSTRACT

The present invention relates to indolopyrolocarbazole derivatives, to their use in methods of treatment or prophylaxis of at least one viral infection or cardiovascular diseases; and pharmaceutical formulations containing such derivatives.

13 Claims, No Drawings

FURTHER INDOLE DERIVATIVES WITH ANTIVIRAL ACTIVITY

This application is a 371 of PCT/GB 93/00571 filed Mar. 19, 1993.

The present invention relates to certain indole derivatives, salts, esters and physiologically functional derivatives thereof, to their use in medical therapy and in particular to their use for the manufacture of a medicament for the treatment or prophylaxis of at least one viral infection.

Of the DNA viruses, those of the herpes group are the sources of the most common viral illnesses in man. The group includes herpes simplex virus (HSV), varicella zoster virus (VZV), cytomegalovirus (CMV); Epstein-Barr virus (EBV) and human herpes virus 6 (HHV6). HSV 1 and HSV 2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can leas to keratitis or cataracts thereby endangering the host's sight. Infection in the newborn, in immunocompromised patients including AIDS patients or penetration of the infection into the central nervous system can prove fatal.

Transmission of the virus is by direct physical contact between a host and a recipient; the spread of HSV infection is therefore considered a very significant social problem, particularly as no effective vaccine is yet available.

Varicella zoster (VZV) is a herpesvirus which causes chickenpox and shingles. Chickenpox is the primary disease produced in a host without immunity and in young children is usually a mild illness characterised by a vesicular rash and fever. Shingles or zoster is the recurrent form of the disease which occurs in adults who were previously infected with varicella-zoster virus. The clinical manifestions of shingles are characterised by neuralgia and a vescicular skin rash that is unilateral and dermatomal in distribution. Spread of inflammation may lead to paralysis or convulsions. Coma can occur if the meninges becomes affected. In immunodeficient patients VZV may disseminate causing serious or even fatal illness. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host and, following a primary infection, virus may be shed for a number of years. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency virus may give rise to retinitis, pneumoitis, gastrointestinal disorders and neurological diseases. CMV infection in AIDS patients is a predominant cause or morbidity as, in 50–80% of the adult population, it is present in a latent form and can be re-activated in immunocompromised patients.

Epstein-Barr virus (EBV) causes infectious mononucleosis and hairy leukoplakis, and is also suggested as the causative agent of human cancer, such as nasopharyngeal cancer, immunoblastic lymphoma, Burkitt's lymphoma.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck.

HBV is a viral pathogen of world-wide major importance. The virus is aetiologically associated with primary hepatocellular carcinoma and is thought to cause 80% of the world's liver cancer. In the United States more than ten thousand people are hospitalised for HBV illness each year, and average of 250 die with fulminant disease. The United States currently contains an estimated pool of 500,000–1-million infectious carriers. Chronic active hepatitis generally develops in over 25% of carriers, and often progresses to cirrhosis. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

Of the RNA viruses, one group has assumed a particular importance. These are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

A species of retrovirus, Human Immunodeficiency Virus (HIV), has been reproducibly isolated from humans with Acquired Immune Deficiency Syndrome (AIDS) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the OKT$^4$ surface marker. HIV is cytopathic and appears to preferentially infect and destroy T-cells bearing the OKT$^4$ marker and it is now generally recognised that HIV is the etiological agent of AIDS.

Another RNA virus which has been recognised as the causative agent of an increasingly serious international health problem is the non-A, non-B hepatitis. At least 80% of cases of chronic post-transfusional non-A, non-B hepatitis have been shown to be due to the virus now identified as hepatitis C and this virus probably accounts for cirtually all cases of post-transfusional hepatitis in clinical settings where blood products are screened for hepatitis B. Whereas approximately half of the cases of acute hepatitis C infection resolve spontaneously over a period of months, the remainder become chronic and in may if not all such cases chronic active hepatitis ensues with the potential for cirrhosis and hepatocellular carcinoma. The structure of the hepatitis C virus genome has recently been elucidated and the virus has been characterised as a single stranded RNA virus with similarities to flaviviruses.

Coxsackie viruses belong to the enterovirus genus. They have a single stranded RNA genome contained in an icosachedral nucleocapsid. Coxsackie virus infection is increasingly recognised as a cause of primary myocardial disease in adults and children. Coxsackie infection is also associated with meningitis, pleurodynia, herpangia, hand-feet and mouth disease, respiratory disease, eye disease, diabetes and post-viral fatigue syndrome. In the latter case viral RNA has been detected in the muscle and in menocytes.

European Patent Specification 0 328 000 describes certain indolecarbazole derivatives and indicates that these compounds can be used for the treatment of heart and blood vessel diseases, such as thromboses, arteriosclerosis and hypertension, inflammatory processes, allergies, cancers and certain degenerative damage to the central nervous system. Maleimide derivatives having similar suggested properties are described in European Patent Specification 0 391 060.

U.S. Pat. No. 5,043,335 describes certain indolecarbazoles and their use in the method of treating heart and blood vessel diseases such as thrombosis, arteriosclerosis and hypertension.

We have now identified certain indole derivatives which have unexpectedly been found suitable for use in the treatment or prophylaxis of viral infections, in particular retrovirus, herpesvirus, hepatitis, coxsackie virus and hepatitis C virus infections.

The present invention therefore lies in the use of the compounds of formula (I)

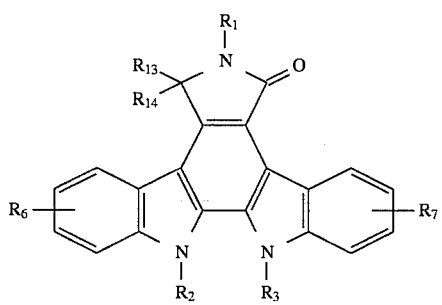

wherein $R^1$ represents:

—H;

—$COR^{10}$, —$COOR^{10}$ where $R^{10}$ is $C_{1-6}$alkyl, $C_{3-7}$cycloalkyl, aryl (for example phenyl), arylalkyl (for example benzyl), $C_{1-6}$alkenyl, or H;

—$OR^{10}$ where $R^{10}$ is as hereinbefore defined.

—$C_{1-8}$alkyl, $C_{1-8}$alkenyl or $C_{3-8}$cycloalkyl where the alkyl, alkenyl or cycloalkyl moiety may be optionally substituted by one or more substituents selected from halogen (for example Cl, Br, F or I), cyano, nitro, azido, $C_{3-8}$cycloalkyl, —$OR^{10}$, —$SR^{10}$, —$SOR^{10}$, —$SO_2R^{10}$, —$NR^{11}R^{12}$ (where $R^{11}$ and $R^{12}$, which may be the same or different, each represent H, —$COR^{10}$ where $R^{10}$ is as hereinbefore defined, $C_{1-6}$alkyl, $C_{3-7}$cycloalkyl, aryl, arylalkyl, tetrahydronaphthyl or indanyl or —$R^{11}R^{12}$ together with the N atom to which they are attached form a 3-,4-,5- or 6- membered heterocyclic ring (for example piperidine, pyrrolidine) in which from 1 to 3 of the carbon atoms may be replaced by heteroatoms independently selected from O, N and S (for example, morpholino, piperazine), the ring being where possible, partially or completely unsaturated, $$-T-\overset{\overset{Z}{\|}}{C}-W$$

(where T is NH or S, Z is NH, S or O and W is $NR^{11}R^{12}$ where $R^{11}$ and $R^{12}$ are each as defined above), non-aromatic heterocycle, —NH-non-aromatic-heterocycle and aryl (for example phenyl, pyridyl, furyl, thienyl, pyrrolo, naphthyl) such heterocycle and aryl groups being optionally substituted by one or more substituents selected from —$OR^{10}$, —$NR^{11}R^{12}$, —$SR^{10}$, —$SOR^{10}$, —$SO_2R^{10}$, —$CO_2R^{10}$, nitro, cyano, SCN, $C_{1-6}$alkyl (wherein one or more hydrogen atoms are optionally replaced by a halogen atom (for example trifluoromethyl)), $C_{3-6}$cycloalkyl, hydroxy$C_{1-6}$alkyl, $CONH_2$, halogen and methylenedioxy, where $R^{10}R^{11}$ and $R^{12}$ are each as defined above;

—$NR^{11}R^{12}$ where $R^{11}$ and $R^{12}$ are each as defined above;

—aryl (for example phenyl) optionally substituted by one or more substituent(s) selected from $OR^{10}$, —$NR^{11}R^{12}$, —$SR^{10}$, —$SOR^{10}$, $SO_2R^{10}$, —$CO_2R^{10}$, nitro cyano, SCN, $C_{1-6}$ alkyl wherein one or more hydrogen atoms are optionally replaced by a halogen atom (for example trifluoromethyl), $C_{3-6}$cycloalkyl, hydroxy$C_{1-6}$alkyl, $CONH_2$, halogen and methylenedioxy, where $R^{10}$, $R^{11}$ and $R^{12}$ are each as defined above;

a cyclic group containing from 3 to 6 carbon atoms in which from 1 to 3 of said atoms may be replaced by heteroatom(s) independently selected from O, S and N (for example thiazole, pyrazole imidazole, triazole, oxazole, piperidine);

—NH—cyclic group containing from 3 to 6 carbon atoms in which from 1 to 3 of said atoms may be replaced by heteroatom(s) independently selected from O, S and N (for example thiazole, pyrazole, imidazole, triazole, oxazole, piperidine);

$R^2$ and $R^3$, which may be the same or different, are each independently selected from:

H;

—$COR^{10}$, —$COOR^{10}$ where $R^{10}$ is $C_{1-6}$alkyl, $C_{3-7}$cycloalkyl, aryl (for example phenyl), arylalkyl (for example benzyl), $C_{1-6}$alkenyl, or H;

—$OR^{10}$ where $R^{10}$ is as hereinbefore defined.

—$C_{1-8}$alkyl, $C_{1-8}$alkenyl or $C_{3-8}$cycloalkyl where the alkyl, alkenyl or cycloalkyl moiety may be optionally substituted by one or more substituents selected from halogen, cyano, nitro, azido, $C_{3-8}$cycloalkyl, —$OR^{10}$, —$COR^{10}$, —$CO_2R^{10}$, —$OCOR^{10}$, —$SR^{10}$, —$SOR^{10}$, —$SO_2R^{10}$, —$CO_2NR^{11}R^{12}$, —$NR^{11}R^{12}$ (where $R^{11}$ and $R^{12}$, which may be the same or different, each represent H, —$COR^{10}$ where $R^{10}$ is as hereinbefore defined, $C_{1-6}$alkyl, $C_{3-7}$cycloalkyl, aryl, arylalkyl, tetrahydronaphthyl or indanyl or —$R^{11}R^{12}$ together with the N atom to which they are attached form a 3-, 4-, 5- or 6- membered heterocyclic ring (for example piperidine, pyrrolidine) in which from 1 to 3 of the carbon atoms may be replaced by heteroatoms independently selected from O, N and S (for example, morpholino, piperazine), the ring being where possible, partially or completely unsaturated, $$-T-\overset{\overset{Z}{\|}}{C}-W$$

(where T is NH or S, Z is NH, S or O and W is $NR^{11}R^{12}$ where $R^{11}$ and $R^{12}$ are each as defined above), non-aromatic heterocycle, —NH-non-aromatic-heterocycle and aryl (for example phenyl, pyridyl, furyl, thienyl, pyrrole, naphthyl)

such heterocycles and aryl groups being optionally substituted by one or more substituents selected from —OR$^{10}$, —NR$^{11}$R$^{12}$, —SR$^{10}$, —SO$_2$R$^{10}$, —CO$_2$R$^{10}$, nitro, cyano, SCN, C$_{1-6}$alkyl (wherein one or more hydrogen atoms are optionally replaced by a halogen atom (for example trifluoromethyl)), C$_{3-6}$cycloalkyl, hydroxyC$_{1-6}$alkyl, CONH$_2$, halogen and methylenedioxy, where R$^{10}$R$^{11}$ and R$^{12}$ are each as defined above;

—NR$^{11}$R$^{12}$ where R$^{11}$ and R$^{12}$ are each as defined above;

—aryl (for example phenyl) optionally substituted by one or more substituent(s) selected from OR$^{10}$, —NR$^{11}$R$^{12}$, SR$^{10}$, —SOR$^{10}$, —SO$_2$R$^{10}$, CO$_2$R$^{10}$, nitro cyano, SCN, C$_{1-6}$alkyl (wherein one or more hydrogen atoms are optionally replaced by a halogen atom (for example trifluoromethyl)), C$_{3-6}$cycloalkyl, hydroxyC$_{1-6}$alkyl, CONH$_2$, halogen and methylenedioxy, where R$^{10}$, R$^{11}$ and R$^{12}$ are each as defined above;

R$^6$ and R$^7$, which may be the same or different, each represent one or more ring substituent(s) selected from:

H;

C$_{1-6}$alkyl optionally substituted by one or more substituents independently selected from halogen (for example trifluoromethyl), —NR$^{11}$R$^{12}$, cyano, —OR$^{10}$, azido, —SR$^{10}$, —SOR$^{10}$, SO$_2$R$^{10}$ wherein R$^{10}$, R$^{11}$ and R$^{12}$ are as hereinbefore defined.

cyano, nitro, halogen, methylenedioxy, —OR$^{10}$, —SR$^{10}$, —SOR$^{10}$, —SO$_2$R$^{10}$, —NHSO$_2$R$^{10}$, —SO$_2$NR$^{11}$R$^{12}$, —CO$_2$R$^{10}$, CONR$^{11}$R$^{12}$, OCOR$^{10}$, and —NR$^{11}$R$^{12}$ where R$^{10}$, R$^{11}$ are as defined above; p R$^{13}$ and R$^{14}$ together form a carbonyl group (>=0) or R$^{13}$ is X and R$^{14}$ is Y and X and Y are both H, or one of X and Y is H and the other is —OR$^{10}$ or —SR$^{10}$, wherein R$^{10}$ is as hereinbefore defined;

or a salt, ester or physiologically functional derivative thereof or a solvate or any thereof, for the manufacture of a medicament for the treatment or prophylaxis of at least one viral infection. Such viral infections include a retrovirus infection, such as HIV, a herpes virus infection, such as those mentioned above and more particularly CMV, VZV, HSV1, HSV2 and an HBV infection.

The present invention also provides the use of the compounds of formula (I) for the manufacture of a medicament for the treatment or prophylaxis of a coxsackie virus or hepatitis C virus infection.

According to one embodiment, the invention provides the use compounds of formula (I) wherein R$^1$ represents:

—H;

—COR$^{10}$, —COOR$^{10}$ where R$^{10}$ is C$_{1-6}$alkyl, C$_{3-7}$cycloalkyl, aryl (for example phenyl), arylalkyl (for example benzyl), C$_{1-6}$alkenyl, or H;

—C$_{1-8}$alkyl, C$_{1-8}$alkenyl or C$_{3-8}$cycloalkyl where the alkyl, alkenyl or cycloalkyl moiety may be optionally substituted by one or more substituents selected from halogen, cyano, nitro, azido, —OR$^{10}$, —SR$^{10}$, —SO$_2$R$^{10}$, —NR$^{11}$R$^{12}$ (where R$^{11}$ and R$^{12}$, which may be the same or different, each represent H, —COR$^{10}$ where R$^{10}$ is as hereinbefore defined, C$_{1-6}$alkyl, C$_{3-7}$cycloalkyl, aryl, arylalkyl, tetrahydronaphthyl or indanyl or —R$^{11}$R$^{12}$ together with the N atom to which they are attached form a 3-,4-,5- or 6- membered heterocyclic ring (for example piperidine, pyrrolidine) in which form 1 to 3 of the carbon atoms may be replaced by heteroatoms independently selected from O, N and S (for example, morpholino, piperazine) which ring may where possible, be partially or completely unsaturated),

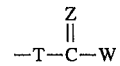

(where T is NH or S, Z is NH, S or O and W is NR$^{11}$R$^{12}$ where R$^{11}$ and R$^{12}$ are each as defined above), heterocycle, —N—heterocycle and aryl (for example phenyl, pyridyl, furyl, thienyl, pyrrolo, naphthyl) optionally substituted by one or more substituents selected from —OR$^{10}$, —NR$^{11}$R$^{12}$, —SR$^{10}$, —SO$_2$R$^{10}$, —CO$_2$R$^{10}$, nitro, cyano, SCN, C$_{1-6}$alkyl, C$_{3-6}$ cycloalkyl, haloalkyl (for example trifluoromethyl), hydroxylalkyl, CONH$_2$, halogen and methylenedioxy, where R$^{10}$R$^{11}$ and R$^{12}$ are each as defined above;

—NR$^{11}$R$^{12}$ where R$^{11}$ and R$^{12}$ are each as defined above;

—aryl (for example phenyl) optionally substituted by one or more substituent(s) selected from —OR$^{10}$, —NR$^{11}$R$^{12}$, —SR$^{10}$, —SO$_2$R$^{10}$, —CO$_2$R$^{10}$, nitro, cyano, SCN, C$_{1-6}$alkyl, C$_{3-6}$cycloalkyl, haloalkyl, hydroxylalkyl, CONH$_2$, halogen and methylenedioxy, where R$^{10}$, R$^{11}$ and R$^{12}$ are each as defined above;

a cyclic group containing 3 to 6 carbon atoms in which from 1 to 3 of said atoms may be replaced by heteroatom(s) independently selected from O, S and N (for example thiazole, pyrazole imidazole, triazole, oxazole, piperidine);

—NH—cyclic group containing from 3 to 6 carbon atoms in which from 1 to 3 of said atoms may be replaced by heteroatom(s) independently selected from O, S and N (for example thiazole, pyrazole, imidazole, triazole, oxazole, piperidine);

R$^2$ and R$^3$, which may be the same or different, are each independently selected from:

H;

—COR$^{10}$, —COOR$^{10}$ where R$^{10}$ is C$_{1-6}$alkyl, C$_{3-7}$cycloalkyl, aryl (for example phenyl), arylalkyl (for example benzyl), C$_{1-6}$alkenyl, or H;

—C$_{1-8}$alkyl, C$_{1-8}$alkenyl or C$_{3-8}$cycloalkyl where the alkyl, alkenyl or cycloalkyl moiety may be optionally substituted by one or more substituents selected from halogen, cyano, nitro, azido, —OR$^{10}$, —SR$^{10}$, —SO$_2$R$^{10}$, —NR$^{11}$R$^{12}$ (where R$^{11}$ and R$^{12}$, which may be the same or different, each represent H, —COR$^{10}$ where R$^{10}$ is as hereinbefore defined, C$_{1-6}$alkyl, C$_{3-7}$cycloalkyl, aryl, arylalkyl, tetrahydronaphthyl or indanyl or —R$^{11}$R$^{12}$ together with the N atom to which they are attached form a 3-,4-,5- or 6- membered heterocyclic ring (for example piperidine, pyrrolidine) in which from 1 to 3 of the carbon atoms may be replaced by heteroatoms independently selected from O, N and S (for example, morpholino, piperazine) which ring may where possible, be partially or completely unsaturated;

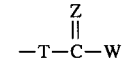

(where T is NH or S, Z is NH, S or O and W is NR$^{11}$R$^{12}$ where R$^{11}$ and R$^{12}$ are each as defined above), heterocycle, —NH—heterocycle and aryl (for example phenyl, pyridyl, furyl, thienyl, pyrrole, naphthyl) optionally substituted by one or more substituents selected from —OR$^{10}$, —NR$^{11}$R$^{12}$, —SR$^{10}$, —SO$_2$R$^{10}$, —CO$_2$R$^{10}$, nitro, cyano, SCN, C$_{1-6}$alkyl, C$_{3-6}$ cycloalkyl, haloalkyl (for example trifluoromethyl), hydroxylalkyl, CONH$_2$, halogen and methylenedioxy, where R$^{10}$, R$^{11}$ and R$^{12}$ are each as defined above;

—NR$^{11}$R$^{12}$ where R$^{11}$ and R$^{12}$ are each as defined above;

—aryl (for example phenyl) optionally substituted by one or more substituent(s) selected from —OR$^{10}$, —NR$^{11}$R$^{12}$, —SR$^{10}$, —SO$_2$R$^{10}$, —CO$_2$R$^{10}$, nitro, cyano, SCN, C$_{1-6}$alkyl, C$_{3-6}$ cycloalkyl, haloalkyl, hydroxylalkyl, CONH$_2$, halogen and methylenedioxy, where R$^{10}$, R$^{11}$ and R$^{12}$ are each as defined above;

R$^6$ and R$^7$, which may be the same or different, each represent one or more ring substituent(s) selected from:

H;

C$_{1-6}$alkyl optionally substituted by OH or halogen (for example trifluoromethyl);

cyano, nitro, halogen, methylenedioxy, —OR$^{10}$, —SR$^{10}$, —SO$_2$R$^{10}$, —CO$_2$R$^{10}$ and —NR$^{11}$R$^{12}$ where R$^{10}$, R$^{11}$ and R$^{12}$ are as defined above and R$^{13}$ and R$^{14}$ are as hereinbefore defined; or a salt, ester or physiologically functional derivative thereof or a solvate or any thereof, for the manufacture of a medicament for the treatment or prophylaxis of a viral infection.

The invention further provides the use of compounds of formula (I) as defined above in which R$^1$ is H and R$^{13}$ and R$^{14}$ are X and Y where X and Y are both hydrogen, or one of X and Y is H and the other is —OR$^{10}$ where R$^{10}$ is H or C$_{1-6}$ alkyl, for the manufacture of a medicament for the treatment or prophylaxis of at least one viral infection, particularly those viral infections described above.

According to a preferred embodiment the invention provides the use of compounds of formula (I) as defined above wherein R$^{13}$ and R$^{14}$ together form a carbonyl group; or a salt, ester or physiologically functional derivative thereof or a solvate of any thereof, for the manufacture of a medicament for the treatment or prophylaxis of at least one viral infection, for example, a herpes virus, retrovirus, HBV, coxsackie virus or hepatitis C virus infection.

In a preferred aspect, the present invention provides the use of 12,13-dihydro-5H-indolo[2,3-a]pyrrolo[3,4-c]-carbazole-5,7(6H)-dione, or a salt, ester or physiologically functional derivative thereof or a solvate thereof for the manufacture of a medicament for the treatment or prophylaxis of at least one viral infection, in particular a herpes virus infection, including CMV, HSV1 and 2, VZV, EBV or HHV6.

As used herein, the term "alkyl" as a group or part of a group means a straight or branched chain alkyl group. Such alkyl groups preferably have 1 to 3 carbon atoms. As used herein the term aryl as a group or part of a group includes aromatic heterocycles (such as pyridine, pyrrolo, furyl, thienyl, pyrazolo, imidazolo, thiazolo, isothiazolo, oxazole, isoxazolo, triazolo, tetrazolo, oxadiazolo, thiadiazolo, benzofuryl, benzothienyl, benzimidazolo, benzotriazolo, quinolyl, isoquinolyl and indolyl). The term non-aromatic heterocycle includes groups such as pyrrolidino, piperazino, morpholino, piperidino, tetrahydrofuryl, tetrahydropyranyl, dioxanyl and dithianyl.

The compounds of formula (I) described above and their salts, esters and physiologically functional derivatives and the solvates of any thereof are hereinafter referred to as the compounds according to the invention.

Examples of retroviral infections which may be treated or prevented in accordance with the invention include human retroviral infections such as Human Immunodeficiency Virus (HIV), for example, HIV-1 or HIV-2, and Human T-cell Lymphotropic Virus (HLTV), for example HTLV-I or HTLV-II, infections. The compounds according to the invention are especially useful for the treatment of AIDS and related clinical conditions such as AIDS-related complex (ARC), progressive generalized lymphadenopathy (PGL), Kaposi's sarcoma, thrombocytopenic purpura, AIDS-related neurological conditions, such as multiple sclerosis or tropical paraperesis, and also anti-HIV antibody-positive and HIV-positive conditions, including such conditions in asymptomatic patients.

Examples of other clinical conditions which may be treated in accordance with this invention include those conditions caused by HIV, HSV 1 and 2, VZV, CMV, EBV, HHV6, HBV, coxsackie virus and hepatitis C virus infections as described above.

The present invention further includes a method for the treatment, prophylaxis or prevention of the symptoms or effects of a viral infection in an infected host, for example, a mammal including humans, which comprises administering to said host a therapeutically effective non-toxic amount of a compound according to the invention. According to a particular embodiment of this aspect of the invention, the viral infection is an infection of a retrovirus, for example, HIV, herpes virus including HSV 1 and 2, VZV, CMV, EBV, HHV6, a hepatitis virus including HBV, coxsackie virus or hepatitis C virus.

The present invention also provides compounds of formula (I) as defined above; or a salt, ester or physiologically functional derivative thereof or a solvate of any thereof; with the provisos that:

(a) when R$^1$ is H and R$^{13}$ are X and Y where X and Y are both hydrogen, or one of X and Y is H and the other is —OR$^{10}$ where R$^{10}$ is H or C$_{1-6}$ alkyl then either:

(i) R$^2$ and R$^3$, which may be the same or different, are each independently selected from —COOR$^{10}$ and —C$_{1-8}$ alkyl substituted by one or more substituents selected from —COR$^{10}$, —OCOR$^{10}$, —SR$^{10}$, —SO$_2$R$^{10}$ and R$^{10}$ is as hereinbefore defined, —C$_{3-7}$ cycloalkyl, nitro and aryl; or a salt, ester or physiologically functional derivative thereof or a solvate of any thereof; or (ii) R$^6$ and R$^7$, which may be the same or different, each represent one or more ring substituent(s) selected from —CF$_3$, cyano, —CO$_2$R$^{10}$, —CONR$^{11}$R$^{12}$, —SR$^{10}$, —SOR$^{10}$, —SO$_2$R$^{10}$, —SO$_2$NR$^{11}$R$^{12}$ wherein R$^{10}$, R$^{11}$ and R$^{12}$ are as hereinbefore defined, and C$_{1-6}$alkyl substituted by —OR$^{10}$ wherein R$^{10}$ is as hereinbefore defined; or a salt, ester or physiologically functional derivative thereof or a solvate of any thereof, and (b) such compounds of formula (I) do not include the compounds 12,13-dihydro-5H-indolo[2,3-a]pyrrolo-[3,4-c]carbazole-5,7(6H)-dione and 12,13-dihydro-1,11-dihydroxy-5H-indole[2,3-a]pyrrolo[3,4-c]-carbazole- 5,7(6H)dione;

for use in therapy, more particularly for use as an antiviral agent, hereinafter referred to collectively as compounds of formula (IA).

Examples of compounds of formula (IA) for use in therapy include:

12,13-Dihydro-3,9-dimethoxy-5H-indolo[2,3-a]pyrrolo[3,4-c]carbazole-5,7(6H)dione;

12,13-Dihydro-3,9-dichloro-5H-indolo[2,3-a]pyrrolo[3,4-c]carbazole-5,7(6H)-dione;

12,13-Dihydro-3,9-dibromo-5H-indolo[2,3-a]pyrrolo[3,4-c]-carbazole-5,7(6H)-dione; and 12,13-Dihydro-6-(phenylmethyl)-5H-indolo[2,3-a]pyrrolo[3,4-c]-carbazole-5,7(6H)-dione;

or a salt, ester or physiologically functional derivative thereof or a solvate of any thereof.

In addition to the use of compounds of formula (I) or (IA), in the treatment or prophylaxis of the above viral infections and associated conditions, the compounds may also be used for the treatment or prophylaxis of heart and blood vessel diseases, such as thromboses, arteriosclerosis and hypertension, inflammatory processes, allergies, cancers and certain degenerative damage to the central nervous system.

Certain of the compounds of formula (I) and their salts, esters and physiologically functional derivatives and solvates of any thereof are new compounds and such new compounds and their derivatives are a further aspect of the present invention.

The new compounds are those as defined above for formula (I) or a salt, ester or physiologically functional derivative thereof or a solvate of any thereof, with the provisos that:

(a) when $R^1$ is H and $R^{13}$ and $R^{14}$ together form a carbonyl group then either:

(i) $R^2$ and $R^3$, which may be the same or different, are each independently selected from —COOR$^{10}$ and —C$_{1-8}$alkyl substituted by one or more substituents selected from —COR$^{10}$, —OCOR$^{10}$, —SR$^{10}$, —SOR$^{10}$, —SO$_2$R$^{10}$ and R$^{10}$ is as hereinbefore defined, —C$_{3-7}$cycloalkyl, nitro and aryl; or a salt, ester or physiologically functional derivative thereof or a solvate of any thereof; or (ii) $R^6$ and $R^7$, which may be the same or different, each represent one or more ring substituent(s) selected from CF$_3$, cyano, —CO$_2$R$^{10}$, —CONR$^{11}$R$^{12}$, —SR$^{10}$, —SOR$^{10}$, —SO$_2$R$^{10}$, —SO$_2$NR$^{11}$R$^{12}$ wherein R$^{10}$, R$^{11}$ and R$^{12}$ are as hereinbefore defined, and C$_{1-6}$alkyl substituted by —OR$^{10}$ wherein R$^{10}$ is as hereinbefore defined; or a salt, ester or physiologically functional derivative thereof or a solvate of any thereof; or (iii) notwithstanding (i) and (ii) above the compounds 12,13-dihydro- 2,10-difluoro-5H-indolo[2,3-a]pyrrolo[3,4-c]carbazole- 5,7(6H)-dione and 12,13-dihydro-12-ethyl-5H-indolo-[2,3-a]-pyrrolo[3,4-c]carbazole-5,7(6H)-dione; or a salt, ester or physiologically functional derivative thereof or a solvate thereof are included within the scope of the present invention;

(b) when $R^1$ is H and $R^{13}$ and $R^{14}$ are X and Y where X and Y are both hydrogen, or one of X and Y is H and the other is —OR$^{10}$ where R$^{10}$ is H or C$_{1-6}$ alkyl then either:

(i) $R^2$ and $R^3$ which may be the same or different, are each independently selected from —COOR$^{10}$ and —C$_{1-8}$alkyl substituted by one or more substituents selected from —COR$^{10}$, —OCOR$^{10}$, —SR$^{10}$, —SOR$^{10}$, —SO$_2$R$^{10}$ and R$^{10}$ is as hereinbefore defined, —C$_{3-7}$cycloalkyl, nitro and aryl; or a salt, ester or physiologically functional derivative thereof or a solvate of any thereof; or (ii) $R^6$ and $R^7$, which may be the same or different, each represent one or more ring substituent(s) selected from CF$_3$, cyano, —CO$_2$R$^{10}$, —CONR$^{11}$R$^{12}$, —SR$^{10}$, —SOR$^{10}$, —SO$_2$R$^{10}$, —SO$_2$NR$^{11}$R$^{12}$ wherein R$^{10}$, R$^{11}$ and R$^{12}$ are as hereinbefore defined, and C$_{1-6}$alkyl substituted by —OR$^{10}$ wherein R$^{10}$ is as hereinbefore defined; or a salt, ester or physiologically functional derivative thereof or a solvate of any thereof; and (c) the following compounds are excluded from the scope of the present invention:

5,6,7,13-tetrahydro-7-oxo-12H-indolo[2,3-a]pyrrolo [3,4-a]pyrazole- 12-carboxylic acid, methyl ester;
  12,13-dihydro-6-phenyl-5H-indole[2,3-a]pyrrolo[3,4-c]carbazole- 5,7(6H)-dione;
  12,13-dihydro-1,11-bis(phenylmethoxy)-6-[(phenylmethoxy)methyl]- 5H-indolo[2,3-a]pyrrolo[3,4-c]carbazole-5,7(6H)-dione;
  12,13-dihydro-6-methyl-5H-indolo[2,3-a]pyrrolo[3,4-a]carbazole- 5,7(6H)-dione;
  1,11-dichloro-12,13-dihydro-6-[(phenylmethoxy)methyl]-5H-indolo[2,3-a]pyrrolo[3,4-c]carbazole-5, 7(6H)-dione;
  12,13-dihydro-6-(phenylmethyl)-5H-indolo[2,3-a]pyrrolo[3,4-c]carbazole- 5,7(6H)-dione;
  6,7,12,13-tetrahydro-6-(tetrahydro-2H-pyran-2-yl)-5H-indole-[2,3-a]pyrrolo[3,4-c]carbazol- 5-one; and
  6,7,12,13-tetrahydro-6-(phenylmethyl)-5H-indolo[2,3-a]pyrrolo-[3,4-c]carbazol-5-one;

hereinafter referred to collectively as compounds of formula (IB).

According to one aspect, the invention provides compounds of formula (IB) wherein $R^{13}$ and $R^{14}$ together form a carbonyl group and $R^1$ represents —C$_{1-8}$alkyl having one or more substituents selected from C$_{3-8}$cycloalkyl, —OR$^{10}$ where R$^{10}$ is H and aryl optionally substituted by one or more substituents selected from nitro and C$_{1-6}$alkyl wherein one or more hydrogen atoms are replaced by a halogen atom; or a salt, ester or physiologically functional derivative thereof or a solvate of any thereof; with the exclusion of the compound:

12,13-dihydro-6-(phenylmethyl)-5H-indolo[2,3-a]pyrrolo[3,4-c]-carbazole- 5,7(6H)-dione.

Preferred compounds of formula (IB) include those wherein $R^{13}$ and $R^{14}$ together form a carbonyl group, $R^1$ represents OH, cyclohexylmethyl, pyridylmethyl or phenylmethyl wherein the phenyl ring is substituted by one or more substituents selected from CF$_3$ and nitro; $R^2$ and $R^3$, which may be the same or different, are each independently selected from H, t-butyloxycarbonyl, acetoxypropyl and ethyl; and $R^6$ and $R^7$, which may be the same or different, each represent one or more ring substituent(s) selected from H, halogen and —OR$^{10}$ wherein R$^{10}$ is C$_{1-6}$alkyl, or a salt, ester or physiologically functional derivative thereof or a solvate of any thereof.

Particularly preferred compounds of formula (IB) include:

12,13-Dihydro-6-(cyclohexylmethyl)-5H-indolo-[2,3a] pyrrolo[3,4c]carbazole-5,7(6H)-dione;
  12,13-Dihydro-6-(3-trifluoromethylphenylmethyl)-5H-indolo-[2,3a]pyrrolo[3,4c]carbazole-5,7(6H)-dione;
  12,13-Dihydro-6-(di-3,5-trifluoromethylphenylmethyl)-5H-indolo-[2,3a]pyrrolo[3,4c]carbazole-5,7(6H)-dione;
  12,13-Dihydro-6-(2-pyridylmethyl)-5H-indolo-[2,3a] pyrrolo[3,4c]carbazole-5,7(6H-dione;
  12,13-Dihydro-6-(3-nitrophenylmethyl)-5H-indolo-[2, 3a]pyrrolo[3,4c]carbazole-5,7(6H)-dione;
  12,13-Dihydro-6-(3-trifluoromethylphenylmethyl)-2,10-difluoro-5H-indolo-[2,3a]pyrrolo[3,4c]carbazole-5,7(6H)-dione;
  12,13-Dihydro-2,10-difluoro-5H-indolo-[2,3a]pyrrolo[3, 4c]carbazole- 5,7(6H)-dione;
  12,13-Dihydro-6-(3-trifluoromethylphenylmethyl)-12-(3-acetoxypropyl)- 5H-indolo-[2,3a]pyrrolo[3,4c]carbazole-5,7(6H)-dione;
  12,13-Dihydro-12-(tert-butyloxycarbonyl)-5H-indolo-[2, 3a]pyrrolo[3,4c]carbazole-5,7(6H)-dione;
  12,13-Dihydro-6-(hydroxy)-5H-indolo-[2,3a]pyrrolo[3, 4c]carbazole- 5,7(6H)-dione:

or a salt, ester or physiologically functional derivative or a solvate of any thereof.

A particularly preferred compound according to the present invention is 12,13-dihydro-12-ethyl-5H-indolo-[2,3-a]pyrrolo[3,4-c]carbazole- 5,7(6HO-dione; or a salt, ester or physiologically functional derivative thereof or a solvate thereof.

It will be understood that each of the preferred compounds of formula (IB) above is particularly efficacious in the treatment or prophylaxis of at least one viral infection independently selected from those of HSV1, HSV2, CMV, VZV, EBV, HHV6, HBV, HIV, hepatitis C and coxsackie virus.

As used herein, the term "physiologically functional derivative" means any physiologically acceptable salt, ester, or salt of such ester, of a compound of formula (I) above or any other compound which upon administration to the recipient, is capable of providing (directly or indirectly) such a compound or an antivirally active metabolite or residue thereof. For example, it is within the scope of the invention to replace the H of the OH group at the 5'- position by a potentially hydrolysable group such as acyl or alkyl.

Preferred esters in accordance with the invention include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$ alkyl, or $C_{1-4}$ alkoxy), or amino; sulphonate esters, such as alkyl- or aralkylsulphonyl (for example, methanesulphonyl); amino acid esters (for example, L-valyl or L-isoleucyl); and mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Any reference to any of the above compounds also includes a reference to a physiologically acceptable salt thereof.

Examples of physiologically acceptable salts of the compounds of formula (I) and physiologically acceptable derivatives thereof include salts derived from an appropriate base, such as an alkali metal (for example, sodium), and alkaline earth (for example, magnesium), ammonium and $NX_4^+$ (wherein X is $C_{1-4}$alkyl). Physiologically acceptable salts of an hydrogen atom or an amino group include salts of organic carboxylic acids such as acetic, lactic, tartaric, malic, isethionic, lactobionic and succinic acids; organic sulfonic acids, such as methanesulphonic, ethanesulphonic, benzenesulphonic and p-toluenesulphonic acids, and inorganic acids, such as hydrochloric, sulphuric, phosphoric and sulphamic acids. Physiologically acceptable salts of a compound of an hydroxy group include the anion of said compound in combination with a suitable cation such as $Na^+$, $NH_4^+$ and $NX_4^+$ (wherein X is a $C_{1-4}$ alkyl group).

For therapeutic use, salts of compounds of formula (I) will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

The compounds according to the invention may be employed in combination with other therapeutic agents for the treatment of the above infections or conditions. Examples of such further therapeutic agents include agents that are effective for the treatment of HIV infections or associated conditions, such as 3'-azido-3'-deoxythymidine (zidovudine), other 2',3'-dideoxynucleosides, such as 2',3'-dideoxycytidine, 2',3'-dideoxyadenosine and 2',3'-dideoxyinosine, carbovir, acyclic nucleosides (for example, acyclovir), 2',3'-didehydrothymidine, protease inhibitors, such as, RO 31-8959, oxathiolan nucleoside analogues, such as, cis-1-(2-hydroxymethyl)-1,3-oxathiolan-5-yl)cytosine (BCH-189) interferons, such as α-interferon, renal excretion inhibitors, such as probenicid, nucleoside transport inhibitors, such as dipyridamole, as well as immunomodulators, such as interleukin II and granulocyte macrophage colony stimulating factors, erythropoetin, phosphonoformic acid, soluble $CD_4$ and genetically engineered derivatives thereof. Examples of such further therapeutic agents with are effective for the treatment of HBV infections, include carbovir, oxathiolan nucleoside analogues, such as, cis-1-(2-hydroxymethyl)-1,3-oxathiolan-5-yl)cytosine (BCH-189) and interferons, such as α-interferon. The compound compounds of such combination therapy may be administered simultaneously, in either separate or combined formulations, or at different times, for example sequentially, such that a combined effect is achieved.

The present invention further provides pharmaceutical formulations containing pharmaceutically acceptable compounds according to the invention, also referred to herein as active ingredients, which may be administered for therapy to a mammal including a human ("the recipient") by any suitable route appropriate to the clinical condition to be treated; suitable routes include oral (including buccal and sublingual), rectal, nasal, topical (including buccal, sublingual and transdermal), vaginal and parenteral (including subcutaneous, intramuscular, intravenous and intradermal). It will be appreciated that the preferred route will vary with the condition, weight, age and sex of the recipient, the nature of the infection and the chosen active ingredient.

The amount of a compound according to the invention required for the treatment of each of the above indicated utilities and indications will depend on a number of factors including the severity of the condition to be treated and the identity of the recipient and will ultimately be at the discretion of the attendant physician.

In general, however, for each of these utilities and indications, a suitable, effective dose will be in the range 0.5 to 120 mg per kilogram body weight of the recipient per day, preferably in the range 1 to 90 mg per kilogram body weight per day and most preferably in the range 2 to 60 mg kilogram body weight per day. An optimum dose is about 30 mg per kilogram body weight per day. Unless otherwise indicated all weights of active ingredients are calculated as the parent compounds of the compounds according to the invention. In the case of a salt, ester or physiologically functional derivative of a compound according to the invention or a solvate of any thereof the figures would be increased proportionately. The desired dose is preferably presented as two, three, four, five, six, or more sub-doses administered at appropriate intervals throughout the day. These sub-doses may be administered in unit dosage forms, for example, containing from 1 to 1500 mg, preferably from 5 to 1000 mg, most preferably from 10 to 700 mg of active ingredient per unit dosage form. Alternatively, if the condition of the recipient so requires, the dose may be administered as a continuous infusion.

Ideally, the active ingredient should be administered to achieve peak plasma concentrations of the active compound of from about 0.25 to about 100 μM, preferably from about 0.5 to 70 μM, most preferably from about 1 to 50 μM. This may be achieved, for example, by the intravenous injection of a 0.1 to 5% w/v solution of the active ingredient, optionally in saline, or orally administered, for example, as a tablet, capsule, or syrup containing from about 0.5 to about 100 mg/kg of the active ingredient. Desirable blood levels may be maintained by a continuous infusion to provide from about 0.01 to about 5.0 mg/kg/hour or by intermittent infusions containing from about 0.4 to about 15 mg/kg of the active ingredient.

While it is possible for the active ingredient to be administered alone, it is preferable to present it as a pharmaceutical formulation. The formulations of the present invention comprise at least one active ingredient, as defined above, together with one or more acceptable carriers thereof and, optionally, one or more other therapeutic agents. Each carrier must be "acceptable" in the sense of being compatible with the other ingredients of the formulation and not injurious to the patient.

Formulations of the invention include those suitable for administration by any of the aforementioned routes which may conveniently be presented in unit dosage form and may be prepared by any method well know in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers, or both, and then, if necessary, shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary, or paste or may be contained within liposomes.

A tablet may be made by compression or moulding, optionally with one or more accessory ingredient. Compressed tablets may be prepared by compressing in a suitable machine the active ingredient in a free-flowing form such as a powder or granules, optionally mixed with a binder (for example, povidone, gelatin, hydroxypropylmethyl cellulose), lubricant, inert diluent, preservative, disintegrant (for example, sodium starch glycollate, cross-linked povidone, crossed-linked sodium carboxmethyl cellulose), or a surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile or to be soluble or effervescent when added to liquid. Tablets may optionally be provided with an enteric coating, to provide release in parts of the gut other than the stomach.

Formulations suitable for oral use may also include buffering agents designed to neutralise stomach acidity. Such buffers may be chosen from a variety of organic or inorganic agents such as weak acids or bases admixed with their conjugated salts.

A capsule may be made by filling a loose or compressed powder on an appropriate filling machine, optionally with one or more additives. Examples of suitable additives include binders such as povidone; gelatin, lubricants, inert diluents and disintegrants as for tablets. Capsules may also be formulated to contain pellets or discrete sub-units to provide slow or controlled release of the active ingredient. This can be achieved by extruding and spheronising a wet mixture of the drug plus an extrusion aid (for example microcrystalline cellulose) plus a diluent such as lactose. The spheroids thus produced can be coated with a semipermeable membrane (for example ethyl cellulose, Eudragit WE30D) to produce sustained release properties.

An edible foam or whip formulation ideally comprises: 50–70% of an edible oil, particularly a vegetable oil, including corn oil, peanut oil, sunflower oil, olive oil and soybean oil; 2–10% of one or more surfactants particularly lecithin, polyols, polyol polymer esters including glyceryl fatty acid esters, polyglyceryl fatty acid esters (e.g. decaglycerol tetraoleate), or sorbitan fatty acid esters (e.g. sorbitan monostearate); 1–4% of a propellant which is suitable for ingestion, notably a compressed gas propellant especially nitrogen, nitrous oxide or carbon dioxide, or a gaseous hydrocarbon especially propane, butane or isobutane; 0.5–30% of one or more viscosity modifiers of particle size in the range 10–50 microns in diameter, particularly powdered sugars or colloidal silicon dioxide; and optionally 0.5–1% of one or more suitable, non-toxic colourings, flavourings or sweetners. The active ingredient is preferably present in such formulations in a concentration of 10–46%, advantageously 30%. An edible foam or whip formulation as described above may be prepared in a conventional manner, for example by mixing the edible oil, surfactant(s) and any other soluble ingredients, adding the viscosity modifier(s) and milling the mixture to form a uniform dispersion and suspension. The active ingredient is blended into the milled mixture until evenly dispersed. Finally, a metered quantity of propellant is incorporated to the mixture after said mixture has been measured into a suitable dispensing container.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved in an adhesive or 3) dispersed in a polymer. A suitable concentration of the active compound is about 1% to 35%, preferably about 3% to 15%. As one particular possibility, the active compound may be delivered from the patch by iontophoresis as generally described in Pharmaceutical Research, 3(6), 318 (1986).

Pharmaceutical formulations for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents.

For infections of the eye or other external tissues, for example mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as a water-in-oil base.

If desired, the aqueous phase of the cream base may include, for example, at least 40–45% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may include a compound which enhances absorption or penetration of the active ingredient through the skin or other affected areas. Examples of such dermal penetration enhancers include dimethylsulphoxide and related analogues.

The oily phase of an emulsion formulation according to the invention may comprise merely an emulsifier (otherwise known as an emulgent), but desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent. The ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavoured material, usually sucrose and acacia or tragacanth; pastilles comprising the active ingredient in an inert material such as gelatin and glycerin, or sucrose and acacia; and mouth-washes comprising the active ingredient in a suitable liquid carrier.

Formulations for rectal administration may be presented as a suppository with a suitable base comprising for example cocoa butter or higher fatty alcohol (e.g. hard wax, European Pharmacopoeia) or triglycerides and saturated fatty acids (e.g. Witepsol) or as an enema wherein the active ingredient may be presented in an aqueous or oily solution, an aqueous or oily suspension, an oil-in-water liquid emulsion or water-in-oil liquid emulsion.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oily solutions of the active ingredient.

Suitable formulations for administration by inhalation include fine particle dusts or mists which may be generated by means of various types of metered dose pressurized aerosols, nebulizers or insufflators.

For pulmonary administration via the mouth, the particle size of the powder or droplets is typically in the range 0.5–10 µm, preferably 1–5 µm, to ensure delivery into the bronchial tree. For nasal administration, a particle size in the range 10–500 µm is preferred to ensure retention in the nasal cavity.

Metered dose inhalers are pressurised aerosol dispensers, typically containing a suspension or solution formulation of the active ingredient in liquefied propellant. During use these devices discharge the formulation through a valve adapted to deliver a metered volume, typically from 10–150 µl, to produce a fine particle spray containing the active ingredient. Suitable propellants include propane and butane, certain chlorofluorocarbon compounds, commonly referred to as "CFS's", for example, dichlorodifluoromethane, trichlorofluoromethane, dichlorotetrafluoroethane, or mixtures thereof. The formulation may additionally contain co-solvents, for example ethanol, surfactants such as oleic acid or sorbitan trioleate, antioxidants and/or suitable flavouring agents.

Nebulizers are commercially available devices that transform solutions or suspensions of the active ingredient into an aerosol therapeutic mist either by means of acceleration of a compressed gas through a narrow venturi orifice, typically air or oxygen, or by means of ultrasonic agitation. Suitable formulations for use in nebulizers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example methylhydroxybenzoate, antioxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in-situ and the powder either presented to air drawn through the device upon inhalation or alternatively delivered by means of a manually operated pump. The powder employed in the insufflator consists either solely of the active ingredient or of a powder blend comprising the active ingredient, a suitable powder diluent such as lactose, and an optional surfactant. The active ingredient typically comprises from 0.1–100% w/w of the formulation.

Pressurized aerosol formulations for inhalation are preferably arranged so that each metered dose contains from 0.05 to 5 mg of a compound of the invention. Similarly, powder formulations for insufflations are so arranged that each unit dose contains from 0.5 to 50 mg. Solution or suspension formulations for nebulisation are arranged as to deliver doses between 1 and 1500 mg. The compounds according to the invention or formulations thereof may be administered by these devices once or several times daily, with one or several doses, for example three or four, being given on each occasion.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspension which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or sub-dose, as herein above recited, or an appropriate fraction thereof, of an active ingredient.

It should be understood that in addition to the ingredients particularly mentioned above, the formulations of this invention may include other agents conventional in the art having regard to the type of formulation in question, for example those suitable for oral administration may include flavouring agents.

A compound of formula (I) or a salt, ester or physiologically functional derivative thereof or a solvate of any thereof may be prepared by the general methods outlined below.

In the following description the symbols $R^1$, $R^2$, $R^3$, $R^6$, $R^7$, $R^{10}$, $R^{11}$, $R^{12}$, $R^{13}$, $R^{14}$, X and Y have the meanings ascribed to them in formula (I) unless otherwise stated. The symbols $R^4$ and $R^5$ and H and $R^{10'}$ is an alternative value of $R^{10}$.

The compounds of formula (I) may be prepared by a process which comprises:

(A) for the preparation of a compound wherein $R^{13}$ and $R^{14}$ together form a carbonyl group and $R^2$ and $R^3$ are hydrogen, cyclising a compound of formula (VI) or formula (VIII)

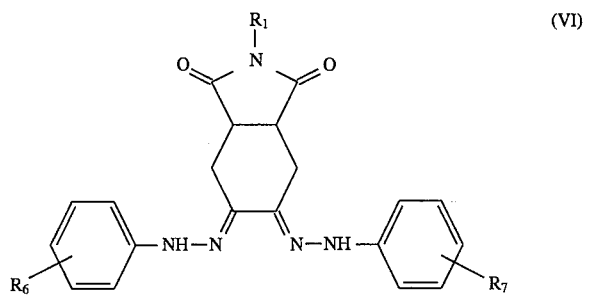

(VI)

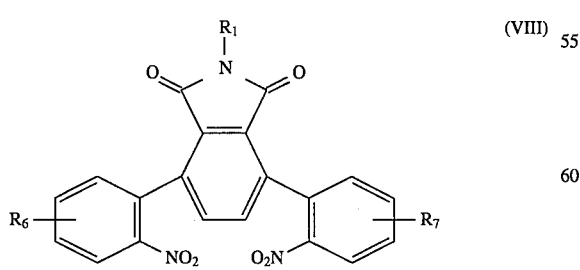

(VIII)

(B) for the preparation of a compound wherein $R^{13}$ and $R^{14}$ together form a carbonyl group and $R^2$ and $R^3$ are hydrogen, by oxidation of a compound of formula (VII)

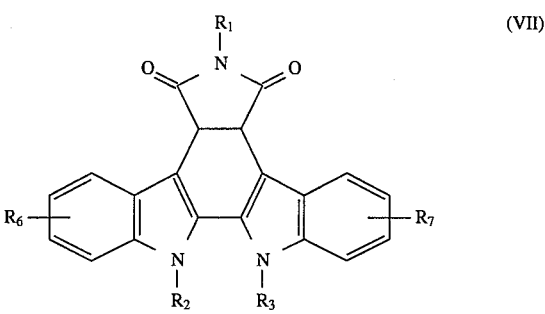

(VII)

(C) for the preparation of a compound wherein $R^{13}$ and $R^{14}$ together form a carbonyl group, cyclising a compound of formula (XVI)

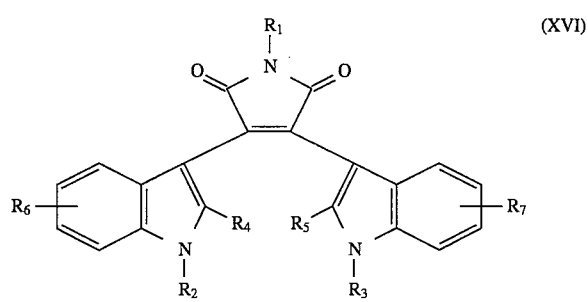

(XVI)

(D) for the preparation of a compound wherein $R^{13}$ and $R^{14}$ together form a carbonyl group, by reacting a compound of formula (IX)

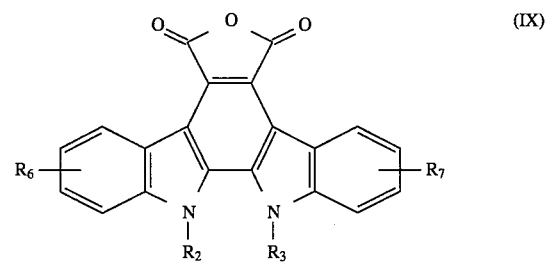

(IX)

with an amine of formula $R^1NH_2$ or $R^1NH_3X^1$ where $X^1$ represents an acid anion.

(E) for the preparation of a compound wherein X is H and Y is OH, by reducing a compound of formula (I) wherein $R^{13}$ and $R^{14}$ together form a carbonyl group, and optionally converting the compound so formed to a compound wherein X and Y are both H.

(F) for the preparation of a compound wherein X is H and Y is $-OR^{10}$ or $-SR^{10}$, by treating a compound of formula (I) wherein X is H and Y is OH, $-OR^{10'}$ or $SR^{10'}$ with a compound $R^{10}OH$ or $R^{10}SH$; and thereafter, or simultaneously therewith, effecting one or more of the following optional conversion:

(i) when the compound of formula (I) is formed, converting it into another compound of formula (I) having different values of $R_2$, $R_3$, $R_6$ and $R_7$ by treatment with an appropriate reagent and/or under suitable conditions;

(ii) removing any remaining protecting groups;

(iii) when the compound of formula (I) is formed, converting it into a pharmaceutically acceptable derivative thereof;

(iv) when the pharmaceutically acceptable derivative of a compound of formula (I) is formed, converting the said derivative into a compound of formula (I), or a different derivative thereof.

According to another aspect, the present invention provides a process for the preparation of a compound of formula (IB); or a salt, ester or physiologically functional derivative thereof or a solvate of any thereof in accordance with the processes described above for the preparation of compounds of formula (I) or a salt, ester or physiologically functional derivative thereof or a solvate of any thereof.

Compounds of formula (I) wherein X, Y are H,H may be prepared in a conventional manner by reacting a compound of formula (I) wherein X, Y are H, —OR¹⁰ with an appropriate reducing agent, for example zinc-amalgam in the presence of acid, Raney-nickel, a metal hydride such as lithium aluminium hydride or diisobutylaluminium hydride, or alternatively with an acid, (for example trifluoroacetic) and a silane (such as triethylsilane).

Alternatively compounds of formula (I) wherein X, Y and both H and R₂ and R₃ are hydrogen may be prepared by reacting compounds of formula (V)

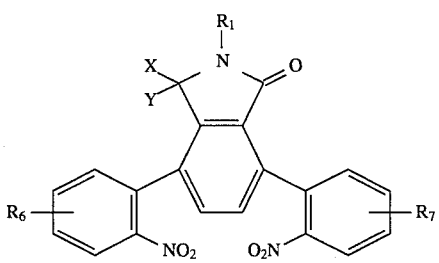

wherein X, Y are H,H with a phosphine or phosphite, for example triphenylphosphine or triethylphosphite.

Compounds of formula (I) wherein X, Y are H, —OR¹⁰ or H, —SR¹⁰ may be prepared from compounds of formula (I) wherein X, Y are H, OH, or H,OR¹⁰ or H,SR¹⁰, by reaction with an, alcohol R¹⁰—OH or a thiol R¹⁰—SH in the presence of an acid such as HCL or TFA.

Compounds of formula (I) wherein X, Y are H, OH can be prepared from compounds of formula (I) wherein R¹³ and R¹⁴ together form a carbonyl group, by reacting with a reducing agent, for example metal hydrides such as lithium aluminium hydride, sodium cyanoborohydride, or by reaction with zinc-amalgam in the presence of aqueous acid.

Alternatively, compounds of formula (I) wherein X, Y are H, OR¹⁰ may be prepared by reacting compounds of formula (I) wherein R¹³ and R¹⁴ together form a carbonyl group, with zinc-amalgam in the presence of acid such as hydrochloric acid and an alcohol R¹⁰OH, preferably in excess.

Compounds of formula (I) wherein R¹³ and R¹⁴ together form a carbonyl group, are typically prepared by reacting a compound of formula (VI)

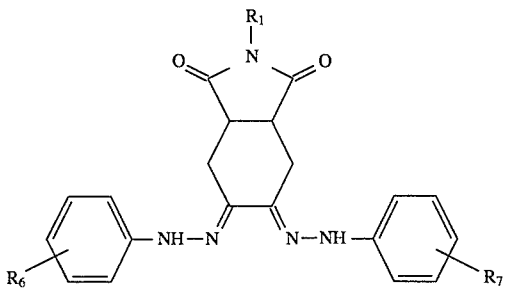

with a suitable reagent such as BF₃-etherate, an acid, for example hydrochloric acid or a Lewis acid, for example zinc bromide, but preferably polyphosphoric acid trimethylsilyl ester, in a suitable solvent, for example nitromethane.

Compounds of formula (I) may also be prepared by treating the corresponding compound of formula (VII)

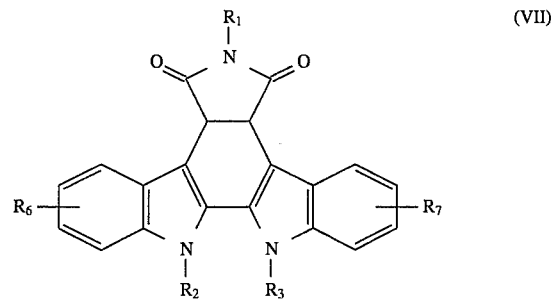

with an oxidising agent such as 2,3-dichloro-5,6-dicyanobenzoquinone, palladium, silver oxide or other oxidising agents such as tert-butyl hypochlorite.

Compounds of formula (VII) wherein R² and R³ are hydrogen may be prepared by reacting a compound of formula (VI) with a suitable reagent such as BF₃-etherate, an acid, a Lewis acid, and most preferably with polyphosphoric acid trimethylsilyl ester, in a suitable solvent, for example nitromethane.

Compounds of formula (VI) may be prepared by methods described by J. Bergman and B. Pelcman, J. Org. Chem. (1989) 54, 824–828.

Compounds of formula (I) wherein R¹³ and R¹⁴ together form the carbonyl group and R², R³ are hydrogen may also be prepared by reacting compounds of formula (VIII)

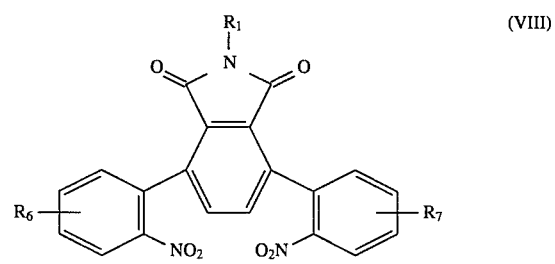

with a phosphine or phosphate, for example triphenylphosphine or a phosphite, for example triethylphosphite, in a suitable solvent such as collidine, lutidine or t-butylbenzene.

Compounds (V) and (VIII) may be prepared according to the methods described by I. Hughes et al. *JCS Perkin* 1 (1990), 2475.

Compounds of formula (I) may also conveniently be prepared by reacting commercially available amines of formula R¹N₂ or amine salts of formula R¹NH₃X¹ where X¹ represents an acid anion such as halide, acetate, carbonate or sulphate with anhydrides of formula (IX)

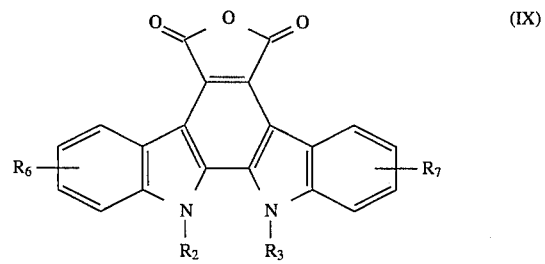

Compounds of formula (IX) may be prepared by reacting a compound of formula (X) where $R_4$ and $R_5$ are hydrogen

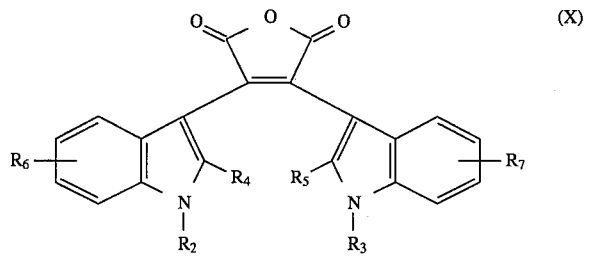

with an oxidising agent such as DDQ (2,3-dichloro-5,6-dicyano-1,4-benzoquinone) in a suitable solvent, such as benzene, toluene, dioxane or xylene, or combinations thereof, preferably in the presence of an acid, for example p-toluenesulphonic acid, and at an elevated temperature, preferably in the range 50°–150° C. Alternatively, cyclisation can be effected using palladium, silver oxide, light optionally with iodine and air, heat or oxidising agents such as tert-butyl hypochlorite.

Compounds of formula (IX) may be prepared by the methods demonstrated in J. Bergman and B. Pelcman, Tetrahedron Letts. (1987) 28, 4441–4444.

Compounds of formula (X) can be prepared by reacting an indole of formula (XI) with an indole of formula (XII)

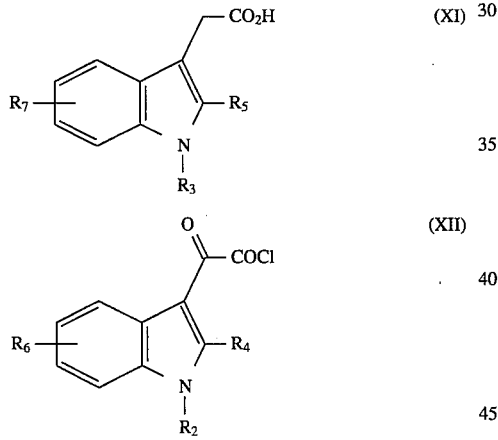

in the presence of a base, such as triethylamine, ethyl diisopropylamine or pyridine and optionally a suitable solvent, such as dichloromethane.

Compounds of formula (XII) may conveniently be prepared by reacting compounds of formula (XIII)

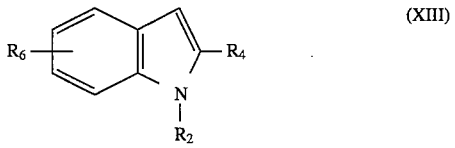

with oxalyl chloride, optionally in a suitable solvent, for example dichloromethane or tetrahydrofuran.

Compounds of formula (XI), (XII) and (XII) may be obtained commercially or prepared by methods well known to a skilled person.

Alternatively, compounds of formula (X) may be prepared by the methods demonstrated in J. Bergman and B. Pelcman, Tetrahedron Letters (1987) 28, 4441–4444.

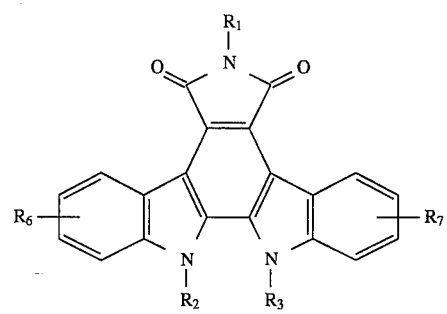

Compounds of formula (III) may be prepared by reacting a compound of formula (XVI) where $R_4$ and $R_5$ are hydrogen

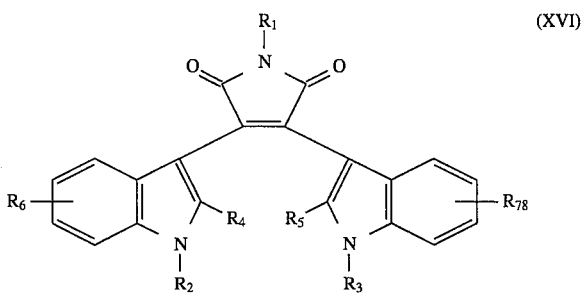

with an oxidising agent such as DDQ (2,3-dichloro-5,6-dicyano-1,4-benzoquinone) in a suitable solvent, such as benzene, toluene, dioxane or xylene, or combinations thereof, preferably in the presence of an acid, for example p-toluenesulphonic acid, and at an elevated temperature, preferably in the range 50°–150° C. Alternatively, cyclisation can be effected using palladium, silver oxide, light, preferably with oxygen and iodine, heat or oxidising agents such as tert-butyl hypochlorite.

Compounds of formula (XVI) may be prepared by reacting compounds of formula (X) with an amine of formula $R^1NH_2$ ($R^1$ as previously defined) or amine salt of formula $R^1NH_3X^{1-}$ ($X^1$ signifies an acid anion such as halide, carboxylate, carbonate or sulphate), optionally in a suitable solvent for example tetrahydrofuran, dimethylformamide, acetic acid or toluene (or combinations thereof), or with hexamethyldisilazane and methanol in a suitable solvent such as tetrahydrofuran or dimethylformamide.

Compounds of formula (XVI) may also conveniently be prepared by reacting compounds of formula (XVII) with a compound of formula (XIX)

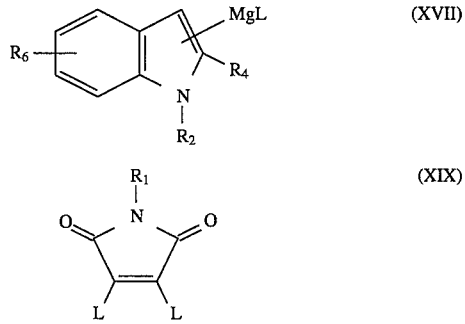

wherein L is a leaving group such as halogen, in a suitable solvent for example tetrahydrofuran, 1,4-dioxane, diethyl ether, benzene, toluene, or combinations thereof at 25°–140° C. (preferably 50°–100° C.) over 30 mins. to 4 days (preferably 1–18 hours).

Compounds of formula (XVII) may be prepared by methods described in Brenner et al, Tetrahedron (1988) 44, 2887–2892.

Compounds of formula (XVI) may also be prepared by reacting compounds of formula (XX)

$$(XX)$$

wherein L is a leaving group such as halogen, with compounds of formula (XVII) in a suitable solvent for example tetrahydrofuran, 1,4-dioxane, benzene, toluene, diethyl ether, or combinations thereof.

Compounds of formula (XX) may be prepared by reacting compounds of formula (XIX) with compounds of formula (XVII) in a suitable solvent such as tetrahydrofuran, 1,4-dioxane, diethyl ether, benzene, toluene, or combinations thereof.

Compounds of formula (XIX) may be prepared by reacting an amine of formula $R^1NH_2$ with a maleic anhydride of formula (XXI)

$$(XXI)$$

wherein L is a leaving group as hereinbefore defined. Compounds of formula (XXI) may be obtained commercially or prepared by methods well known in the art.

It will be appreciated that when $R^1$, $R^2$, $R^3$ are protecting groups, they may be introduced or removed at any stage of the process according to methods known in the art (Theodora W. Greene and Peter G. M. Wuts in Protecting Groups in Organic Syntheses (2nd Ed), 1991, Wiley and Sons). Preferred protecting groups for the indole nitrogen are tert-butyloxycarbonyl (BOC), p-toluenesulphonyl (tosyl), benzyl, benxyloxymethyl, methoxy and silyl (e.g. tert-butyldimethylsily, triisopropyl).

The introduction of groups $R^2$ and $R^3$ where $R^2$ and/or $R^3$ are not hydrogen may be performed at any stage of the process. For example the indole nitrogens may be alkylated or acylated with groups $R^2$—L or $R^3$—L where $R^2$ and $R^3$ are as previously defined with the exception of hydrogen, and L is a suitable leaving group such as halogen or sulphonate ester (e.g. trifluoromethanesulphonate). The reaction preferably taking place in the presence of a base (e.g. triethylamine), or a metal hydride (e.g. sodium hydride), or an alkyl lithium (e.g. n-butyl lithium), and in a suitable solvent (such as dimethylformamide, tetrahydrofuran, dimethylsulphoxide).

The introduction of groups $R^6$ and $R^7$ where $R^6$ and/or $R^7$ are not hydrogen, may be performed at any stage, according to methods known in the art of indole chemistry and aromatic chemistry. For example, a halogen atom may be conveniently introduced using N-halosuccinimides or by the use of a halogen (J.Org.Chem (1951) 16, 1198). A nitro group may for example, be introduced using $KNO_3$ or $HNO_3$ in the presence of sulphuric acid or using nitronium tetrafluoroborate. Acyl (e.g. formyl) or sulphonyl groups may, for example, be introduced by methods described in Chem. Ind. (1981), 338 and J.Amer.Chem.Soc. (1946) 68, 1272 respectively.

Compounds of formula (I) may be converted into an ester by reaction with an appropriate esterifying agent, for example, an acid halide or anhydride. Where it is desired to isolate a compound of formula (I) as an acid addition salt, for example a physiologically acceptable acid addition salt, the salt may be formed by reacting the compound of formula (I) in the form of the free base with the appropriate acid. The two reactants are preferably used in equivalent amounts and the reaction may be carried out in a suitable solvent such as an alcohol, for example ethanol, an ester, for example ethyl acetate, or an ether, for example tetrahydrofuran. One salt of a compound of formula (I) may be converted into another salt using standard methods, for example where it is desired to convert a salt of a compound of formula (I) with an acid which is not physiologically acceptable into a salt with a physiologically acceptable acid. An ester or salt may be converted into the parent compound, for example, by hydrolysis.

The compounds of formula (XVI) wherein $R^1$ represents OH, cyclohexylmethyl, pyridylmethyl or phenylmethyl wherein the phenyl ring is substituted by one or more substituents selected from $CF_3$ and nitro; or cyclohexyl, $R^2$ and $R^3$, which may be the same; or different, are each independently selected from H, t-butyloxycarbonyl, acetoxypropyl and ethyl; $R^4$ and $R^5$ are hydrogen and $R^6$ and $R^7$, which may be the same or different, each represent one or more ring substituent(s) selected from H, halogen and —$OR^{10}$ wherein $R^{10}$ is $C_{1-6}$alkyl; or a salt, ester or physiologically functional derivative thereof or a solvate of any thereof are a further feature of the present invention.

Particularly preferred compounds of formula (XVI) include:

3,4-Bis(1H-indol-3-yl)-2,5-dihydro-1-(3-trifulorophenylmethyl-1H-pyrrolo-2,5-dione;

3,4-Bis-(1H-indol3-yl)-2,5-dihydro-1-(cyclohexylmethyl)-1H-pyrrolo-2,5-dione;

3,4-Bis-(1H-indol-3-yl)-2,5-dihydro-1-(2-pyridylmethyl)-1H-pyrrolo-2,5-dione hydrochloride;

3,4-Bis(1H-indol-3-yl)-2,5-dihydro-1-(3-nitrophenylmethyl)-1H-pyrrolo-2,5-dione;

3,4-Bis(1H-indol-3-yl)-2,5-dihydro-1-(3,5-di-trifluoromethylphenylmethyl)-1H-pyrrolo- 2,5-dione;

3-(1-(3-Hydroxypropyl)-1H-indol-3-yl)-4-(1H-indol-3-yl)-2,5-dihydro-1-( 3-trifluoromethylphenyl methyl)-1H-pyrrolo-2,5-dione;

3,4-Bis(6-fluoro-1H-indol-3-yl)-2,5-dihydro-1-(3-trifluoromethylphenylmethyl)- 1H-pyrrolo-2,5-dione;

12,13-Dihydro-6-(benzyloxy)-5H-indolo[2,3a]pyrrolo-[3,4c]carbazole-5,7(6H)-dione;

1,12-Di-tert-butyloxycarbonyl-12,13-dihydro-5H-indolo[2,3a]pyrrolo-[3,4c]carbazole-5,7-(6H)-dione;

The following Examples are intended for illustration only and are not intended to limit the scope of the invention in any way. The term "active ingredient" as used in the Examples means a compound of formula (I) or a salt, ester or physiologically functional derivative of a compound of formula (I) or a solvate of any thereof.

EXPERIMENTALS

General Methods for the Preparation of N-Substituted-3,4-dichloromaleimides

Method A

Examples 1–5 below

To a solution of dichloromaleic anhydride (20 g, 0.12 mol) in acetic acid (60 ml) was added the amine (0.12 mol, 1.0 equivalent commercially available) dropwise with stirring and cooling (ice/water bath). The mixture was then heated under reflux for 30–480 mins. (preferably 90–180 mins.) After cooling, water (100 ml) was added and the resulting precipitate filtered off and purified by recrystallisation or sublimation. If the imide did not precipitate, EtOAc was added and the organic layer separated, dried ($Na_2SO_4$) and evaporated. The residue was redissolved in EtOAc, washed with aqueous sodium bicarbonate solution, separated, dried ($Na_2SO_4$) and evaporated. The residue was purified by crystallisation, sublimation, or flash chromatography over silica.

The following compounds were thus prepared.

Example 1

3,4-Dichloro-2,5-dihydro-1-(3-trifluoromethylphenylmethyl)-1H-pyrrolo-2,5-dione (1) M.p. 82.5°–83.5° C.

Anal. $C_{12}H_6Cl_2F_3NO_2$ requires C, 44.47%, H, 1.87%, N, 4.32% C, 44.36%, H, 1.82%, N, 4.44%

Example 2

3,4-Dichloro-2,5-dihydro-1-(2-pyridylmethyl)-1H-pyrrolo-2,5-dione (2) M.p. 55°–56° C.

Example 3

3,4-Dichloro-2,5-dihydro-1-methyl-1H-pyrrolo-2,5-dione (3) M.p. 82°–83° C.

Anal. $C_5H_3Cl_2NO_2$ requires C, 33.36%, H, 1.68%, N, 7.78% Found C, 33.04%, H, 1.65%, N, 7.62%

Example 4

3,4-Dichloro-2,5-dihydro-1-(phenylmethyl)-1H-pyrrolo-2,5-dione (4) M.p. 11°–114° C.

Anal. $C_{11}H_7Cl_2NO_2$ requires C, 51.59%, H, 2.76%, N, 5.47% Found C, 51.30%, H, 2.69%, N, 5.36%

Example 5

3,4-Dichloro-2,5-dihydro-1-(cyclohexylmethyl)-1H-pyrrolo-2,5-dione (5) M.p. 80°–82° C.

Anal. $C_{11}H_{13}Cl_2NO_2.0.1\ H_2O$ requires C, 50.04%, H, 5.00%, N, 5.31% Found C, 49.90%, H, 5.08%, N, 5.35%

General Method for the Preparation of 3-Chloro-2,5-dihydro-4-(1H-indol-3-yl)-1H-pyrrole-2,5-diones and 3,4-bis-(1H-indol-3-yl)-2,5-Dihydro-1H-pyrrole-2,5-diones described in Examples 6–10 below To a solution of ethyl magnesium bromide (57 mmol) in THF (25 ml) under nitrogen was added a solution of the indole (57 mmol) in benzene (35) over 40 mins. at 0° C. with stirring. The solution was then stirred for a further 5–60 mins. or optionally heated at 50° C. for 10–200 mins. The 3,4-dichloromaleimide derivative (14 mmol) in benzene or benzene/THF (35 ml) was then added dropwise over 20–60 mins. at room temperature with stirring. The solution was then heated under reflux for 30 mins. to 4 days (usually 60–480 mins.). After cooling, the mixture was quenched with 20% w/v citric acid solution or ammonium chloride solution. Ethyl acetate was added, the organic layer separated, washed with water, dried ($Na_2SO_4$) and evaporated. The residue was then flash chromatographed over silica, eluting with a suitable solvent system (e.g. ether/hexane, ethyl acetate/hexane, dichloromethane). The first coloured compound to be eluted was the 3-chloro-2,5-dihydro-4-(1H-indol-3-yl)-1H-pyrrolo-2,5-dione, followed by the 3,4-bis-(1H-indol-3-yl)-2,5-dihydro-1H-pyrrole-2,5-dione.

The following examples were thus prepared.

Example 6

3,4-Bis(1H-indol-3yl)-2,5-dihydro-1-(3-trifluorophenylmethyl)-1H-pyrrolo-2,5-dione (6) M.p. 233°234° C.

Anal. $C_{28}H_{11}F_3N_3O_2$ requires C, 69.28%, H, 3.74%, N, 8.60% Found C, 69.40%, H, 3.80%, N, 8.56%

Example 7

3,4-Bis-(1H-indol-3yl)-2,5-dihydro-1-(cyclohexylmethyl)-1H-pyrrolo-2,5-dione (7) M.p. 240°–242° C.

Anal. $C_{27}H_{25}\ N_3O_2.0.33H_2O$ requires C, 75.54%, H, 5.98%, N, 9.79% Found C, 75.70%, H, 6.03%, N, 9.46%

Example 8

3,4-Bis-(1H-indol-3-yl)-2,5-dihydro-1-(2-pyridylmethyl)-1H-pyrrolo-2,5-dione hydrochloride (8)

The hydrochloride salt was prepared by dissolving the parent compound in THF, on addition of chloroform previously saturated with hydrogen chloride gas, the salt precipitated and was isolated by filtration. M.p. decomposes above 100° C.

Example 9

3,4-Bis-(6-fluoro-1H-indol-3-yl)-2,5-dihydro-1-(methyl)-1H-pyrrolo-2,5-dione (9) M.p. 274°–276° C.

Anal. $C_{21}H_{13}F_2N_3O_2.0.13CH_3CO_2C_2H_5$ requires C, 66.48%, H, 3.64%, N, 10.81% Found C, 66.35%, H, 3.53%, H, 3.53%, N, 10.78%

Example 10

3,4-Bis-(1H-indol-3-yl)-2,5-dihydro-1-methyl-1H-pyrrolo-2,5-dione (10) M.p. 272°–277° C. Reference: J. Med. Chem. (1992) 35, 177–184

General Method for the Preparation of 3,4-Bis-(1H-indol-3-yl) maleic anhydrides A solution of the 3,4-bis(1-H-indolo-3-yl)-2,5-dihydro-1-methyl-1H-pyrrolo-2,5-dione in 10% aqueous potassium hydroxide and a co-solvent, preferably dioxane or methanol, was heated under reflux for 1–30 hours. When tlc analysis ($SiO_2$) revealed the absence of starting material, the mixture was cooled and acidified. If the product precipitated at this stage, it could be isolated by filtration and optionally crystallised. Alternatively, the product could be extracted, for example with ethyl acetate, and then purified by crystallistion or column chromatography over silica.

The following examples were thus prepared.

Example 11

3,4-Bis-(1H-indol-3-yl) maleic anhydride (11) M.p. 125°–129° C.

Anal. $C_{20}H_{12}N_2O_3.0.75H_2O$ requires C, 70.27%, H, 3.98%, N, 8.22% Found C, 70.43%, H, 4.17%, N, 8.20%

Example 12

3,4-Bis (6-fluoro-1H-indol-3-yl) maleic anhydride (12) M.p. 291°–292° C.

Anal. $C_{20}H_{21}F_2N_2O_3.0.55CH_3COC_3H_5$ requires C, 64.06%, H, 3.52%, N, 6.79% Found C, 64.79%, H, 3.71%, N, 6.64%

General Method for the Preparation of 1-Unsubstituted-3,4-bis-(1H-indol-3-yl)-2,5-dihydro-1H-pyrrolo-2,5-diones from 3,4-bis (1H-indol-3-yl) maleic anhydrides A mixture of the 3,4-bis-(1H-indol-3-yl) maleic anhydride and an excess of ammonium acetate (typically 10–250 equivalents) were heated at 140° until reaction was complete (typically 15–240 mins). The mixture was then cooled, partitioned between ethyl acetate and water (brine, aqueous HCl or bicarbonate solution may be used), and the organic phase separated. After further washings, the organic phase is dried (MgSO$_4$) and evaporated. The product may then be recrystallised or purified by flash chromatography over silica. The following examples were thus prepared.

Example 13

3,4-Bis (6-fluoro-1H-indol-3-yl)-2,5-dihydro-1H pyrrolo-2,5-dione (13) M.p. 281°–282° C.

Anal. $C_{20}H_{11}F_2N_3O_2.1.2CH_3CO_2H_5$ requires C, 63.45%, H, 4.45%, N, 8.91% Found C, 63.18%, H, 4.19%, N, 9.09%

General Method for the Preparation of 1-Substituted-2,5-dihydro-3,4-bis-( 1H-indol-3-yl)-1H-pyrrolo-2,5-diones from 3,4-Bis-(1H-indol-3-yl) maleic anhydrides A solution of the 3,4-Bis-(1H-indol-3-yl)-maleic anhydride in a suitable solvent, such as acetic acid, tetrahydrofuran, toluene, dimethylformamide (or combinations thereof), in combination with excess of the amine (2–10 equivs) or an excess of the amine salt and an appropriate base (e.g. ethyldiisopropylamine, potassium carbonate), was heated at 70°–150° C. until tlc revealed that most of the anhydride had been consumed. The solvent was then optionally evaporated in vacuo, the residue partitioned between an organic solvent (e.g. ethyl acetate) and aqueous acid (e.g. HCl, acetic acid) or aqueous base (e.g. sodium bicarbonate solution), the organic layer separated, dried (MgSO$_4$) and evaporated. Alternatively, the reaction mixture may optionally be partitioned directly by the addition of aqueous acid or base, the organic layer separated, dried (MgSO$_4$) and evaporated. The product may then be purified by crystallisation or flash chromatography over silica.

The following examples were thus prepared.

Example 14

3,4-Bis-(1H-indol-3-yl)-2,5-dihydro-1-benzyloxy-1H-pyrrolo-2,5-dione (14) M.p. 204°–205° C.

Anal. $C_{27}H_{19}N_3O_3$ requires C, 74.81%, H, 4.42%, N, 9.70% Found C, 74.79%, H, 4.59%, N, 9.54%

Example 15

3,4-Bis(1H-indol-3-yl)-2,5-dihydro-1-(3-nitrophenylmethyl)-1H-pyrrolo-2,5-dione (15) M.p. 182°–185° C.

Anal. $C_{27}H_{18}N_4O_4$ requires C, 70.10%, H, 3.93%, N, 12.12 % Found C, 70.08%, H, 3.90%, N, 11.97 %

Example 16

3,4-Bis(1H-indol-3-yl)-2,5-dihydro-1-(3,5-di-trifluormethylphenyl methyl)-1H-pyrrolo-2,5-dione (16) M.p. 185°–186° C.

Anal. $C_{29}H_{17}F_6N_3O_2.0.5_2H_2O$ requires C, 61.91%, H, 3.23%, N, 7.47% Found C, 62.04%, H, 3.14%, N, 7.17%

Example 17

3,4-Bis(6-fluoro-1H-indol-3-yl)-2,5-dihydro-1-(3-trifluoromethylphenyl)-1H-pyrrolo- 2,5-dione (17) M.p. 251°–252° C.

Anal. $C_{28}H_{16}F_5N_3O_2$ requires C, 64.50%, H, 3.09%, N, 8.06% Found C, 64.18%, H, 3.16%, N, 8.18%

Example 18

3-(1-(3-Acetoxypropyl)-1H-indol-3-yl)-4-(1H-indol-3yl)-2,5-dihydro- 1-(3-trifluoromethylphenyl methyl)-1H-pyrrolo-2,5-dione (18)

Prepared from example 20. The reaction mixture was acidified with acetic acid, the, when acetylation was complete (tlc), the mixture partitioned using ethyl acetate and water, and the organic layer separated. After washing with water, drying (MgSO$_4$) and evaporation, the product (18) was purified using flash chromatography over silica (hexane/ethyl acetate (2:1)). M.p. 80° C.

Anal. $C_{33}H_{26}F_3N_3O_4.0.25H_2O$ requires C, 67.18%, H, 4.50%, N, 7.12% Found C, 67.39%, H, 4.45%, N, 6.83%

Preparation of 3,4-Bis(1(3-hydroxypropyl)-1H-indol-3-yl)-maleic anhydride (19) and 3(1-[3-hydroxypropyl)-1H-indol-3-yl)-4-( 1H-indol-3-yl)-maleic anhydride (20)

To a solution of 10 (5.11 g, 15 mmol) in dry DMF (45 ml) at 0° C. under nitrogen was added sodium hydride (60% dispersion in mineral oil, 660 mg, 165 mmol) and the mixture stirred at room temperature for 30 minutes. The mixture was cooled to −10° C., and 3-chloropropyl acetate (2.05 g, 15 mmol) added. The mixture was stirred at room temperature overnight, then evaporated to dryness and taken up in ethyl acetate. After washing with brine, and drying, (MgSO$_4$) the solvent was evaporated and the residue chromatographed over flash silica (hexane/ethyl acetate, (1:1). The coloured fractions were pooled, evaporated and dissolved in a mixture of 10% KOH solution (40 ml) and dioxane (20 ml). The mixture was heated under reflux for 15 hours, cooled, and acidified with concentrated hydrochloric acid. The mixture was then extracted three times with ethyl acetate, washed with water, dried (MgSO$_4$) and evaporated. Flash chromatography over silica, eluting with hexane/ethyl acetate (1:3), gave 20 as the first eluted product. M.P. 100° C. (dec.)

Anal. $C_{23}H_{18}N_2O_4.0.66H_2O$ requires C, 69.37%, H, 4.86%, N, 7.04% Found C, 69.20%, H, 4.65%, N, 6.85%

The second eluted product was 19.

M.p. 128°–130° C.

Anal. $C_{26}H_{24}N_2O_5.1H_2O$ requires C, 67.53%, H, 5.63%, N, 6.06% Found C, 67.59%, H, 5.47 %, N, 5.97%

General Method for the Preparation of 12,13-Dihydro-5H-indolo[2,3a]-pyrrolo[3,4c]carbazole-5,7(6H)-diones described in Examples 21–28 below To a solution of the 3,4-Bis(1H-indol-3-yl)-2,5-dihydro-1H-pyrrolo-2,5-dione derivative in xylene, toluene, or dioxane, or combinations thereof at 100°–140° C. was added 2,3-dichloro-5,6-dicyanobenzoquinone (1.1equivalents) and p-toluenesulphonic acid (0.01–1.2 equivalents). The mixture was maintained at this temperature until TLC monitoring indicated that the reaction was complete (usually 1–60 mins.). The mixture was then cooled. If the product precipitated, it was isolated by filtration and recrystallisation. Otherwise sodium bicarbonate solution was added and the organic layer separated, dried ($Na_2SO_4$) and evaporated. Some examples can be purified by recrystallisation at this stage. Otherwise the products were purified by flash chromatography over silica or basic alumina (eluted with hexane, ethyl acetate, acetone, THF, or combinations thereof).

The following compounds were thus prepared.

Example 21

12,13-Dihydro-6-(cyclohexylmethyl)-5H-indol[2,3a]pyrrolo[3,4c]-carbazole- 5,7(6H)-dione (21) M.p. 342° C. (dec)

Anal. $C_{27}H_{23}N_3O_2 \cdot CH_3CO_2C_2H_5$ requires C, 73.08%, H, 6.09%, N, 8.25% Found C, 72.77%, H, 6.24%, N, 8.17%

Example 22

12,13-Dihydro-6-(3-trifluoromethylphenylmethyl)-5H-indolo[2,3a]pyrrolo[3,4c]-carbazole- 5,7-(6H)-dione (22)

M.p. >300° C.

Anal. $C_{28}H_{16}F_3N_3O_2 \cdot 1.5H_2O$ requires C, 65.88%, H, 3.75%, N, 8.23% Found C, 65.79%, H, 3.57%, N, 8.29%

Example 23

12,13-Dihydro-6-(3,5-di-trifluoromethylphenylmethyl)-5H-indolo [2,3a]pyrrolo[3,4c]carbazole-5,7(6H)-dione (23) M.p. 305°–307° C.

Anal. $C_{29}H_{15}F_6N_3O_2 \cdot 0.5H_2O$ requires C, 62.12%, H, 2.88%, N, 7.50% Found C, 62.16% H, 2.88%, N, 7.29%

Example 24

12,13-Dihydro-2,10-difluoro-5H-indolo[2,3a]pyrrolo[3,4c]carbazole-5,7-(6H)-dione (24) M.p. >300° C.

Anal. $C_{20}H_9F_2N_3O_2 \cdot 0.74CH_3CO_2C_2H_5$ requires C, 64.66%, H, 3.53%, N, 9.85% Found C, 64.48%, H, 3.34%, N, 9.93%

Example 25

12,13-Dihydro-3,9-dimethoxy-5H-indolo[2,3a]pyrrolo[3,4c]carbazole-5,7(6H)-dione (25) M.p. >320° C.

Anal. $C_{22}H_{15}N_3 \cdot 0.8H_2O$ requires C, 66.09%, 3.78%, N, 10.51% Found C, 66.28%, H, 3.72%, N, 10.49%

Example 26

12,13-Dihydro-2,10-difluoro-6-(3-trifluoromethylphenylmethyl)-5H-indolo[2,3a]pyrrolo[3,4c]carbazole-5,7(6H)-dione (26) M.p. >300° C. Mass spec: $M^+$ (519)

Example 27

Prepared from the compound described in Example 18. 12,13-Dihydro-12-(3-acetoxypropyl)-6-(3-trifluoromethylphenylmethyl)-5H-indolo[2,3a]pyrrolo[3,4c]-carbazole-5,7(6H)-dione (27) M.p. 85° C. (dec)

Anal. $C_{33}H_{24}F_3N_3O_4 \cdot 0.125CCl_4$ requires C, 66.00%, H, 3.99%, N, 6.97% Found C, 66.01%, H, 3.96%, N, 6.89%

Example 28

12,13-Dihydro-6-(3-nitrophenylmethyl)-5H-indolo[2,3a]pyrrolo[3,4c]-carbazole- 5,7(6H)-dione (28) M.p. 344°–347° C.

Anal. $C_{27}H_{16}N_4O_4 \cdot 0.7H_2O$ requires C, 68.53%; H, 3.70%; N, 11.85% Found C, 68.64%; H, 3.52%; H, 3.52%; N, 11.29%

Example 29

Preparation of 12,13-Dihydro-6-(2-pyridylmethyl)-5H-indolo[2,3-a]-pyrrolo[3,4-c]carbazolo-5,7(6H)-dione (29)

A solution of 8 (100 mg, 0.26 mmol) and sodium perborate (158 mg) was heated under reflux in acetic acid (4 ml) for 8 hours. The solution was then diluted with ethyl acetate, washed with sodium bicarbonate solution, the organic phase separated and dried ($Na_2SO_4$). The product was chromatographed over silica containing 10% basic alumina, eluting with EtOAc (containing 1% $Et_3N$). The fractions containing the product were combined, and from these the crude product crystallised out. Final purification by HPLC, (gradient, 0–95% MeCN in $H_2O$ over 15 mins, with 1% TFA), gave the pure product 29 as a yellow solid. Mass spec: M+1 417

Example 30

Preparation of 12,13-Dihydro-6-(benzyloxy)-5H-indolo[2,3a]pyrrolo-[3,4c]carbazle-5,7(6H)-dione (31)

To a solution of 14 (485 mg, 1.12 mmol) in toluene (120 ml) at 110° C. was added silver (I) oxide (570 mg, 2.2 eq) and the mixture heated at 110° C. for five hours. The precipitate was then filtered off and washed well with THF (–150 ml). The filtrates were combined, evaporated, and triturated with ethyl acetate. The residual orange solid was the pure product (30). M.p. >310° C.

Anal. $C_{27}H_{17}N_3O_3 \cdot 0.5H_2O$ requires C, 73.62%, H, 4.12%, N, 9.54% Found C, 73.84%, H, 3.92%, N, 9.39%

Example 31

Preparation of 12,13-Dihydro-6-(hydroxy)-5H-indol[2,3a]pyrrolo[3,4c]-carbazole-5,7(6H)-dione (31)

A mixture of 30 (140 mg, 0.32 mmol), 10% palladium on carbon (100 mg), THF (110 ml) and acetic acid (20 ml) was hydrogenated at room temperature for 3 hours. The mixture was then filtered through hyflo, the catalyst washed with ethyl acetate/ethanol (3:1, –100 ml), the filtrates combined and evaporated. Recrystallisation from ethyl acetate afforded the product (31) as a dark orange solid. M.p. 295°–300° C. (dec)

Anal. $C_{20}H_{11}N_3O_3 \cdot 1.3H_2O$ requires C, 65.85%, H, 3.75%, H, 11.52% Found C, 65.96%, H, 3.44%, N, 11.22%

Example 32

Preparation of
12-tert-Butyloxycarbonyl-12,13-dihydro-5H-indolo[2,3a]pyrrolo[3,4c]carbazole-5,7(6H)-dione (32A) and 1,12-Di-tert-butyloxycarbonyl-12,13-dihydro-5H-indol[2,3a]pyrrolo[3,-4c]carbazole-5,7(6H)-dione (32B)

To a solution of 12,13-dihydro-5H-indolo[2,3a]pyrrolo[3,4c]carbazole-5,7(6H)-dione (97.5 mg, 0.3 mmol), (J.Org.Chem (1989) 54, 824) in dry DMF (7.5 ml) at 0° C. under nitrogen was added sodium hydride (60% dispersion in mineral oil, 14.4 mg). After stirring for 40 minutes, the mixture was cooled to −10° C. and a solution of di-tert-butyl dicarbonate (79 mg, 0.36 mmol) in dry DMF (1 ml) was added. The mixture was then stirred at room temperature overnight. Following dilution with water, the mixture was neutralised with glacial acetic acid and extracted twice with dichloromethane. The combined organic extracts were washed with water, dried ($MgSO_4$), evaporated, and chromatographed over flash silica (eluant:$CH_2Cl_2$, then $CH_2Cl_2$/MeOH (99:1)).

The first eluted product was 32B. M.p. >360° C.

Anal. $C_{30}H_{27}N_3O_6 \cdot 0.33H_2O$ required C, 67.80%, H, 5.21%, N, 7.90% Found C, 67.57%, H, 5.11%, N, 7.75 %

The second eluted product was 32A M.p. >360° C.

Anal. $C_{25}H_{19}N_3O_4$ requires C, 70.59%, H, 4.47%, N, 9.88% Found C, 70.28%, H, 4.54%, N, 9.95%

Example 33

Preparation of
12-Ethyl-12,13-dihydro-5H-indolo[2,3a]pyrrolo[3,4c]carbazole-5,7(6H)-dione (33)

To a suspension of 32B (2.63 mg, 0.5 mmol) in dry DMF (20 ml) at 0° C. under nitrogen was added sodium hydride (60% dispersion in mineral oil, 24 mg, 0.6 mmol). After stirring for 30 minutes, the mixture was cooled to −10° C., ethyl iodide (80 μl) was added, and the mixture stirred overnight at room temperature. The solution was diluted with water, the resulting precipitate filtered off and chromatographed over flash silica, eluting with hexane/ethyl acetate (4:1). Fractions containing the 12-ethyl derivative were collected, evaporated, and dissolved in ethyl acetate (10 ml) at 0° C. Ethyl acetate (previously saturated with HCl gas, 5 ml) was added, and the mixture stirred at room temperature for 2.5 days. The product (33) precipitated and was isolated by filtration, washed with ether and dried in vacuo. M.p. 350° C. (dec)

Anal. $C_{22}H_{15}N_3O_2 \cdot 0.75H_2O$ required C, 72.03%, H, 4.50%, N, 11.46% Found C, 72.10%, H, 4.35%, N, 11.20%

Examples

The following examples illustrate pharmaceutical formulations according to the invention to which the active ingredient is a pharmaceutically acceptable compound according to the invention.

Example 34

Tablet Formulations

The following formulations A, B and C are prepared by wet granulation of the ingredients with a solution of povidone, followed by addition of the magnesium stearate and compression.

| Formulation A | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |

| Formulation B | mg/tablet | mg/tablet |
|---|---|---|
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |

| Formulation C | mg/tablet |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients.

| Formulation D | mg/capsule |
|---|---|
| Active Ingredient | 250 |
| Pregelatinised Starch NF15 | 150 |
| | 400 |

| Formulation E | mg/capsule |
|---|---|
| Active Ingredient | 250 |
| Lactose | 150 |
| Avicel | 100 |
| | 500 |

Formulation F (Controlled Release Formulation)

The formulation is prepared by wet granulation of the following ingredients with a solution of povidone followed by addition of the magnesium stearate and compression.

| | mg/tablet |
|---|---|
| (a) Active Ingredient | 500 |
| (b) Hydroxypropylmethylcellulose (Methocel K4M Premium) | 11 |
| (c) Lactose B.P. | 53 |
| (d) Povidone B.P.C. | 28 |
| (e) Magnesium Stearate | 7 |
| | 700 |

Drug release takes place over a period of about 6–8 hours and is complete after 12 hours.

Example 35

Capsule Formulations

Formulation A

A capsule formulation is prepared by admixing the ingredients of Formulation D in Example 3 above and filling into two-part hard gelatin capsule.

| Formulation B | mg/capsule |
| --- | --- |
| (a) Active ingredient | 250 |
| (b) Lactose B.P. | 143 |
| (c) Sodium Starch Glycollate | 25 |
| (d) Magnesium Stearate | 2 |
| | 420 |

Capsules are prepared by admixing the above ingredients and filling into two-part hard gelatin capsules.

| Formulation C | mg/capsule |
| --- | --- |
| (a) Active ingredient | 250 |
| (b) Macrogol 4000 BP | 350 |
| | 600 |

Capsules are prepared by melting the Macrogel 4000 BP, dispersing the active ingredient in the melt and filling the melt into two-part hard gelatin capsules.

| Formulation D | mg/capsule |
| --- | --- |
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controling membrane (d) and filled into two-piece, hard gelatin capsules.

| | mg/capsule |
| --- | --- |
| (a) Active Ingredient | 250 |
| (b) Microcrystalline Cellulose | 125 |
| (c) Lactose BP | 125 |
| (d) Ethyl Cellulose | 13 |
| | 513 |

Example 36

Injectable Formulation

| Formulation A | |
| --- | --- |
| Active ingredient | 0.200 g |
| Hydrochloric acid solution, 0.1 M | q.s. to pH 4.0 to 7.0 |
| Sodium hydroxide solution, 0.1 M | q.s. to pH 4.0 to 7.0 |
| Sterile water | q.s. to 10 ml |

The active ingredient is dissolved in most of the water (35°–40° C.) and the pH adjusted to between 4.0 and 7.0 using the hydrochloric acid or the sodium hydroxide as appropriate. The batch is then made up to volume with the water and filtered through a sterile micropore filter into a sterile amber glass vial 10 ml and sealed with sterile closures and overseals.

| Formulation B | |
| --- | --- |
| Active ingredient | 0.125 g |
| Sterile, pyrogen-free, pH 7 phosphate buffer, | q.s. to 25 ml |

Example 37

| Intramuscular injection | |
| --- | --- |
| Active Ingredient | 0.20 g |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is then added and dissolved, and water addd to 3 ml. The mixture is then filtered through a sterile micropore filter and sealed in sterile amber glass vials 3 ml.

Example 38

| Syrup | |
| --- | --- |
| Active ingredient | 0.25 g |
| Sorbitol Solution | 0.10 g |
| Glycerol | 2.00 g |
| Sodium Benzoate | 0.005 g |
| Flavour, Peach 17.42.3169 | 0.0125 ml |
| Purified Water | q.s. to 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

Example 39

| Suppository | mg/suppository |
| --- | --- |
| Active Ingredient | 250 |
| Hard Fat, BP (Witepsol H15 - Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 20 g of the mixture is filled into suitable, 2 ml plastic moulds. The suppositories are allowed to cool to room temperature.

Example 40

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

Example 41

Antiviral Testing (a) HeLa-CD4$^+$ cell assay for evaluating susceptibility of HIV to antiviral compounds Susceptibility of HIV to inhibitors was determined by infection of HT4-6C cell monolayers as described by Larder, B. A., Chesebro, B. & Richman, D. D. Antimicrob. Agents Chemother. 1990 34, 436–441. Briefly cells were seeded in 24-well multiwells at $5 \times 10^4$ cells per well and incubated overnight at 37° C. in growth medium (DMEM10). Monolayers were infected with 100–200 pfu of cell-free virus in 0.2 ml of DMEM containing 5% fetal bovine serum plus antibiotics (DMEM5) and incubated for 1 hour at 37° C. to allow virus adsorption. Following this time, 0.8 ml of DMEM5 (with or without inhibitor) was added to each well and cultures were incubated at 37° C. for 2–3 days. Monolayers were fixed with 10% formaldehyde solution in PBS and stained with 0.25% crystal violet in order to visualize virus plaques. Individual foci of multinucleated gian cells (plaques) were apparent using this staining procedure. ID$_{50}$ values were derived from plots of percent plaque reduction versus inhibitor concentration.

(b) HSV Assay

Herpes Simplex Virus types 1 (HSV 1) and 2 (HSV 2) were assayed in monolayers of Vero cells in multiwell trays. The virus strains used were SC16 and 186 for HSV-1 and HSV-2 respectively. Activity of compounds was determined in the plaque reduction assay, in which a cell monolayer was infected with a suspension of the appropriate HSV, and then overlaid with nutrient carboxymethyl cellulose in the form of a gel to ensure that there was no spread of virus throughout the culture. A range of concentrations of compound of known molarity was incorporated in the nutrient carboxymethyl cellulose overlay. Plaque numbers at each concentration is expressed as percentages of the control and a dose-response curve was drawn.

(c) CMV assay

Human cytomegalovirus (HCMV) was assayed in monolayers of either MRC5 cells (human embryonic lung) in multiwell trays. The strandard CMV strain AD 169 was used. Activity of compounds is determined in the plaque reduction assay, in which a cell monolayer is infected with a suspension of HCMV, and then overlaid with nutrient carboxymethyl cellulose in the form of a gel to ensure that there is no spread of virus throughout the culture. A range of concentrations of known compound of known molarity was incorporated in the nutrient agarose overlay. Plaque numbers at each concentration of drug are expressed as percentage of the control and a dose-response curve is drawn.

| | CMV IC$_{50}$μM | Cytoxicity CCID$_{50}$μM |
|---|---|---|
| 12,13-Dihydro-6-(3,5-di-trifluoro-methylphenylmethyl)-5H-indolo[2,3a]pyrrolo[3,4c]carbazole-5,7(6H)-dione | 5.7 | >125 |
| 12,13-Dihydro-6-(3-trifluoromethyl-phenylmethyl)-5H-indolo[2,3a]-pyrrolo[3,4c]-carbazole-5,7(6H)-dione | 1.2 | >500 |
| 12,13-dihydro-3,9-dichloro-5H-indolo[2,3-a]pyrrolo[3,4-c]carbazole-5,7(6H)-dione | 0.16 | >125 |

(d) VZV Assay

Clinical isolates of varicella zoster virus (VZV) were assayed in monolayers of MRC-5 cells. MRC-5 cells are derived from human embryonic lung tissue. A plaque reduction assay was used in which a suspension of the virus stock was used to infect monolayers of the cells in multiwell trays. A range of concentrations of the compound under test of known molarity was added to the wells. Plaque numbers at each concentration were expressed as percentages of the control and a dose response curve was constructed. From these curves the 50% inhibitory concentration of each drug was determined.

(e) Cell Toxicity

Cell toxicity is assessed in cell growth inhibition assay. Subconfluent cultures of Vero cells grown on 96-well microtiter dishes are exposed to different dilutions of drug, and cell viability determined daily on replicate cultures using uptake of a tetrazolium dye (MTT). The concentration required for 50% inhibition of cell viability at 96 hours is termed CCID$_{50}$.

We claim:

1. A method of treatment of the symptoms or effects of a viral infection in an infected host which comprises administering to said host a therapeutically effective non-toxic amount of a compound of formula (I)

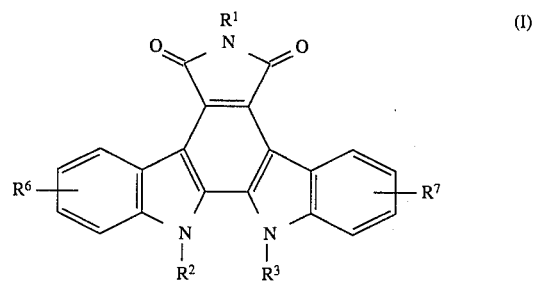

wherein

R$^1$ represents:

—H;

—COR$^{10}$, —COOR$^{10}$ where R$^{10}$ is C$_{1-6}$alkyl, C$_{3-7}$cycloalkyl, aryl, arylalkyl, C$_{1-6}$alkenyl, or H;

—OR¹⁰ where R¹⁰ is as hereinbefore defined;

—$C_{1-8}$ alkyl, $C_{1-8}$ alkenyl or $C_{3-8}$ cycloalkyl where the alky, alkenyl or cycloalkyl moiety may be optionally substituted by one or more substituents selected from halogen, cyano, nitro, azido, $C_{3-8}$cycloalkyl, —OR¹⁰, —SR¹⁰, —SOR¹⁰, —SO₂R¹⁰, —NR¹¹R¹² where R¹¹ and R¹², which may be the same or different, each represent H, —COR¹⁰ where R¹⁰ is as hereinbefore defined, $C_{1-6}$ alkyl, $C_{3-7}$ cycloalkyl, aryl, arylalkyl, tetrahydronaphthyl or indanyl or —R¹¹R¹² together with the N atom to which they are attached form a 3-,4-,5- or 6-membered heterocyclic ring in which from 1 to 3 of the carbon atoms may be replaced by heteroatoms independently selected from O, N and S, the ring being where possible, partially or completely unsaturated,

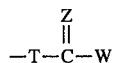

where T is NH or S, Z is NH, S or O and W is NR¹¹R¹² where R¹¹ and R¹² are each as defined above, non-aromatic heterocycle, —NH-non-aromatic-heterocycle and aryl, such heterocycle and aryl groups being optionally substituted by one or more substituents selected from —OR¹⁰, —NR¹¹R¹², —SR¹⁰, —SOR¹⁰, —SO₂R¹⁰, —CO₂R¹⁰, nitro, cyano, SCN, C $C_{1-6}$ alkyl wherein one or more hydrogen atoms are optionally replaced by a halogen atom, $C_{3-6}$ cycloalkyl, hydroxy$C_{1-6}$alkyl, CONH₂, halogen and methylenedioxy, where R¹⁰, R¹¹ and R¹² are each as defined above;

—NR¹¹R¹² where R¹¹ and R¹² are each as defined above;

-aryl optionally substituted by one or more substituents selected from OR¹⁰, —NR¹¹R¹², —SR¹⁰, —SOR¹⁰, —SO₂R¹⁰, —CO₂R¹⁰, nitro, cyano, SCN, $C_{1-6}$ alkyl wherein one or more hydrogen atoms are optionally replaced by a halogen atom, $C_{3-6}$cycloalkyl, hydroxy $C_{1-6}$ alkyl, CONH₂, halogen and methylenedioxy where R¹⁰, R¹¹ and R¹² are each as defined above;

a cyclic group containing from 3 to 6 carbon atoms in which from 1 to 3 of said atoms may be replaced by heteroatoms independently selected from O, S and N;

—NH-cyclic group containing from 3 to 6 carbon atoms in which from 1 to 3 of said atoms may be replaced by heteroatoms independently selected from O, S and N;

R² and R³, which may be the same or different, are each independently selected from:

H;

—COR¹⁰, —COOR¹⁰ where R¹⁰ is $C_{1-6}$alkyl, $C_{3-7}$ cycloalkyl, aryl, arylalkyl, $C_{1-6}$ alkenyl, or H;

—OR¹⁰ wherein R¹⁰ is as hereinbefore defined;

—$C_{1-8}$ alkyl, $C_{1-8}$ alkenyl or $C_{3-8}$ cycloalkyl where the alkyl, alkneyl or cycloalkyl moiety may be optionally substituted by one or more substituents selected from halogen, cyano, nitro, azido, $C_{3-8}$ cycloalkyl, —OR¹⁰, —COR¹⁰, —CO₂R¹⁰, —OCOR¹⁰, —SR¹⁰, —SOR¹⁰, —SO₂R¹⁰, —CO₂NR¹¹R¹², —NR¹¹R¹² where R¹¹ and R¹², which may be the same or different, each represent H, —COR¹⁰ where R¹⁰ is as hereinbefore defined, $C_{1-6}$alkyl, $C_{3-7}$cycloalkyl, aryl, arylakyl, tetrahydronaphthyl or indanyl or —R¹¹R¹² together with the N atom to which they are attached from a 3-,4-,5- or 6-membered heterocyclic ring in which from 1 to 3 of the carbon atoms may be replaced by heteroatoms independently selected from O, N and S, the ring being where possible, partially or completely unsaturated;

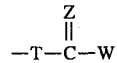

where T is NH or S, Z is NH, S or O and W is NR¹¹R¹² where R¹¹ and R¹² are each as defined above, non-aromatic heterocycle, —NH-non-aromatic-heterocycle and aryl, such heterocycle and aryl groups being optionally substituted by one or more substituents selected from —OR¹⁰, —NR¹¹R¹², —SR¹⁰, —SOR¹⁰, —SO₂R¹⁰, —CO₂R¹⁰, nitro, cyano, SCN, $C_{1-6}$ alkyl, wherein one or more hydrogen atoms are optionally replaced by a halogen atom, $C_{3-6}$ cycloalkyl, hydroxy $C_{1-6}$alkyl, CONH₂, halogen and methylenedioxy, where R¹⁰, R¹¹ and R¹² are each as defined above;

—NR¹¹R¹² where R¹¹ and R¹² are each as defined above;

-aryl optionally substituted by one or more substituents selected from —OR¹⁰, —NR¹¹R¹², SR¹⁰, —SOR¹⁰, —SO₂R¹⁰, CO₂R¹⁰, nitro, cyano, SCN, $C_{1-6}$ alkyl, wherein one or more hydrogen atoms are optionally replaced by a halogen atom, $C_{3-6}$cycloalkyl, hydroxy $C_{1-6}$ alkyl, CONH₂, halogen and methylenedioxy, where R¹⁰, R¹¹, R¹² are each as defined above;

R⁶ and R⁷, which may be the same or different, each represent one or more ring substituents selected from:

H;

$C_{1-6}$alkyl optionally substituted by one or more substituents independently selected from halogen —NR¹¹R¹², cyano, —OR¹⁰, azido, —SR¹⁰, —SOR¹⁰, SO₂R¹⁰, wherein R¹⁰, R¹¹, and R¹² are as hereinbefore defined;

cyano, nitro, halogen, methylenedioxy, —OR¹⁰, —SR¹⁰, —SOR¹⁰, —SO₂R¹⁰, —NHSO₂R¹⁰, —SO₂NR¹¹R¹², —CO₂R¹⁰, CONR¹¹R¹², OCOR and —NR¹¹R¹² where R¹⁰, R¹¹ and R¹² are as define above;

or a salt, ester or physiologically functional derivative thereof or a solvate of any thereof.

2. A method according to claim 1 wherein the virus infection is a CMV infection.

3. A method according to claim 1 wherein R¹ represents —$C_{1-8}$alkyl having one or more substituents selected from $C_{3-8}$cycloalkyl, —OR¹⁰ where R¹⁰ is H and aryl optionally substituted by one or more substituents selected from nitro and $C_{1-6}$alkyl wherein one or more hydrogen atoms are replaced by a halogen atom; or a salt, ester or physiologically functional derivative thereof or a solvate of any thereof.

4. A method according to claim 1 wherein R¹ represents OH, cyclohexylmethyl, pyridylmethyl or phenylmethyl wherein the phenyl ring is substituted by one or more substituents selected from CH₃ and nitro; or cyclohexyl, R² and R³, which may be the same or different, are each independently selected from H, t-butyloxycarbonyl, acetoxypropyl and ethyl; and R⁶ and R⁷, which may be the same or different, each represent one or more ring substituents selected from H, halogen and —OR¹⁰ wherein R¹⁰ is $C_{1-6}$alkyl; or a salt, ester or physiologically functional derivative thereof or a solvate of any thereof.

5. A method according to claim 1 wherein the compound of formula (I) is selected from 12,13-Dihydro-6-(cyclohexylmethyl)-5 H-indolo-[2,3a] pyrrolo-[3,4c]carbazole-5,7(6H)-dione;

12,13-Dihydro-6-(3-trifluoromethylphenylmethyl)-5 H-indolo-[2,3a]-pyrrolo-[3,4c]carbazole-5,7(6H)-dione;

12,13-Dihydro-6-(di-3,5-trifluoromethylphenylmethyl)-5 H-indolo-[2,3a]pyrrolo-[3,4c]carbazole-5,7(6 H)-dione;

12,13-Dihydro-6-(2-pyridylmethyl)-5 H-indolo-[2,3a] pyrrolo-[3,4c]carbazole-5,7(6H)-dione;

12,13-Dihydro-6-(3-nitrophenylmethyl)-5 H-indolo-[2,3a]pyrrolo-[3,4c]carbazole-5,7(6H)-dione;

12,13-Dihydro-6-(3-trilurormethylphenylmethyl)-2,10-difluoro-5 H-indolo-[2,3a]pyrrolo-[3,4c]carbazole-5,7(6 H)-dione;

12,13-Dihydro-2,10-difluoro-5 H-indolo-[2,3a]pyrrolo[3,4c]carbazole-5,7(6H)-dione;

12,13-Dihydro-6-(3-trifluoromethylphenylmethyl)-12-(3-acetoxypropyl)-5 H-indolo[2,3a]-pyrrolo[3,4c]carbazole-5,7(6H)-dione;

12,13-Dihydro-12-(tert-butyloxycarbonyl)-5 H-indolo-[2,3a]pyrrolo-[3,4c]-carbazole-5,7(6H)-dione;

12,13-Dihydro-6-(hydroxy)-5 H-indolo-[2,3a]pyrrolo[3,4c]carbazole-5,7(6H)-dione;

12,13-Dihydro-3,9-dimethoxy-5 H-indolo[2,3-a]pyrrolo[3,4-c]-carbazole-5,7(6H)-dione;

12,13-Dihydro-3,9-dichloroindolo-5 H-[2,3-a]pyrrolo[3,4-c]-carbazole-5,7(6H)-dione;

12,13-Dihydro-3,9-dibromo-5 H-indolo[2,3-a]pyrrolo[3,4-c]-carbazole-5,7(6H)-dione; and 12,13-Dihydro-6-(phenylmethyl)-5 H-indolo[2,3-a]pyrrolo[3,4-c]-carbazole-5,7(6H)-dione;

or salts, esters and physiologically functional derivatives thereof and solvates of any thereof.

6. A method of treatment of the symptoms or effects of heart and blood vessel disease which comprises administering to said host a therapeutically effective non-toxic amount of a compound of formula (I) as defined in claim 1.

7. A compound of formula (I)

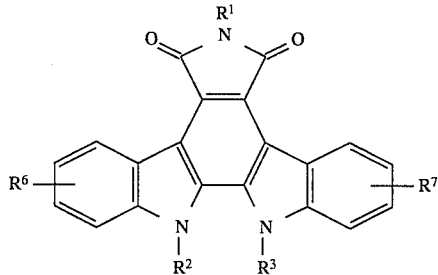

wherein
$R^1$ represents:

—H;

—$COR^{10}$, —$COOR^{10}$ where $R^{10}$ is $C_{1-6}$alkyl, $C_{3-7}$ cycloalkyl, aryl, arylalkyl, $C_{1-6}$ alkenyl, or H;

—$OR^{10}$ where $R^{10}$ is as hereinbefore defined;

—$C_{1-8}$ alkyl, $C_{1-8}$ alkenyl or $C_{3-8}$ cycloalkyl where the alkyl, alkenyl or cycloalkyl moiety may be optionally substituted by one or more substituents selected from halogen, cyano, nitro, azido, $C_{3-8}$cycloalkyl, —$OR^{10}$, —$SR^{10}$, —$SOR^{10}$, —$SO_2R^{10}$, —$NR^{11}R^{12}$ where $R^{11}$ and $R^{12}$, which may be the same or different, each represent H, —$COR^{10}$ where $R^{10}$ is as hereinbefore defined, $C_{1-6}$alkyl, $C_{3-7}$ cycloalkyl, aryl, arylalkyl, tetrahydronaphthyl or indanyl or —$R^{11}R^{12}$ together with the N atom to which they are attached form a 3-,4-,5- or 6-membered heterocyclic ring in which from 1 to 3 of the carbon atoms may be replaced by heteroatoms independently selected from O, N and S, the ring being where possible, partially or completely unsaturated,

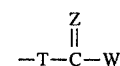

where T is NH or S, Z is NH, S or O and W is $NU^{11}R^{12}$ where $R^{11}$ and $R^{10}$ are each as defined above, non-aromatic heterocycle, —NH-non-aromatic-heterocycle and aryl such heterocycle and aryl, groups being optionally substituted by one or more substituents selected from —$OR^{10}$, —$NR^{11}R^{12}$, —$SOR^{10}$, —$SO_2R^{10}$, —$CO_2R^{10}$, nitro, cyano, SCN, $C_{1-6}$ alkyl wherein one or more hydrogen atoms are optionally replaced by a halogen atom, $C_{3-6}$ cycloalkyl, hydroxy$C_{1-6}$alkyl, $CONH_2$, halogen and methylenedioxy, where $R^{10}R^{11}$ and $R^{12}$ are each as defined above;

—$NR^{11}R^{12}$ where $R^{11}$ and $R^{12}$ are each as defined above;

-aryl optionally substituted by one or more substituents selected from $OR^{10}$, —$NR^{11}R^{12}$, —$SR^{10}$, —$SOR^{10}$, —$SO_2R^{10}$, —$CO_2R^{10}$, nitro, cyano, SCN, $C_{1-6}$alkyl wherein one or more hydrogen atoms are optionally replaced by a halogen atom, $C_{3-6}$cycloalkyl, hydroxy $C_{1-6}$alkyl, $CONH_2$, halogen and methylenedioxy, where $R^{10}$, $R^{11}$ and $R^{12}$ are each as defined above;

a cyclic group containing from 3 to 6 carbon atoms in which from 1 to 3 of said atoms may be replaced by heteroatoms independently selected from O, S and N;

—NH-cyclic group containing from 3 to 6 carbon atoms in which from 1 to 3 of said atoms may be replaced by heteroatoms independently selected from O, S and N;

$R^2$ and $R^3$, which may be the same or different, are each independently selected from:

H;

—$COR^{10}$, —$COOR^{10}$ where $R^{10}$ is a $C_{1-6}$alkyl, $C_{3-7}$ cycloalkyl, aryl, arylalkyl, $C_{1-6}$ alkenyl, or H, —$OR^{10}$ wherein $R^{10}$ is as hereinbefore defined;

—$C_{1-8}$alkyl, $C_{1-8}$ alkenyl or $C_{3-8}$ cycloalkyl where the alkyl, alkenyl or cycloalkyl moiety may be optionally substituted by one or more substituents selected from halogen, cyano, nitro, azido, $C_{3-8}$cycloalkyl, —$OR^{10}$, —$COR^{10}$, —$CO_2R^{10}$, —$OCOR^{10}$, —$SR^{10}$, —$SOR^{10}$, —$SO_2R^{10}$, —$CO_2NR^{11}R^{12}$ where $R^{11}$ and $R^{12}$, which may be the same or different, each represent H, —$COR^{10}$ where $R^{10}$ is as hereinbefore defined, $_{1-6}$alkyl, $C_{3-7}$cycloalkyl, aryl, arylalkyl, tetrahydronaphthyl or indanyl or —$R^{11}R^{12}$ together with the N atom to which they are attached form a 3-,4-,5- or 6-membered heterocyclic ring in which from 1 to 3 of the carbon atoms may be replaced by heteroatoms independently selected from O, N and S, the ring being where possible, partially or completely unsaturated;

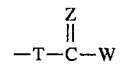

where T is NH or S, Z is NH, S or O and W is $NU^{11}R^{12}$ where $R^{11}$ and $R^{12}$ are each as defined above, non-aromatic heterocycle, —NH-non-aromatic-heterocycle and aryl such heterocycle and aryl, groups being optionally substituted by one or more substituents selected from —$OR^{10}$, —$NR^{11}R^{12}$, —$SR^{10}$, —$SOR^{10}$, —$SO_2R^{10}$, —$CO_2R^{10}$, nitro, cyano, SCN, $C_{1-6}$ alkyl wherein one or more hydrogen atoms are optionally replaced by a halogen atom, $C_{3-6}$ cycloalkyl, hydroxy$C_{1-6}$alkyl, $CONH_2$, halogen and methylenedioxy, where $R^{10}R^{11}$ and $R^{12}$ are each as defined above;
—$NR^{11}R^{12}$ where $R^{11}$ and $R^{11}$ are each as defined above;
-aryl optionally substituted by one or more substituents selected from —$OR^{10}$, —$NR^{11}R^{12}$, $SR^{10}$, —$SOR^{10}$, —$SO_2R^{10}$ $CO_2R^{10}$, nitro, cyano, SCN, $C_{1-6}$alkyl wherein one or more hydrogen atoms are optionally replaced by a halogen atom, $C_{3-6}$cycloalkyl, hydroxy $C_{1-6}$alkyl, $CONH_2$, halogen and methylenedioxy, where $R^{10}$, $R^{11}$ and $R^{12}$ are each as defined above;

$R^6$ and $R^7$, which may be the same or different, each represent one or more ring substituents selected from;

H;

$C_{1-6}$alkyl optionally substituted by one or more substituents independently selected from halogen, —$NR^{11},R^{12}$, cyano, —$OR^{10}$, azido, —$SR^{10}$, —$SOR^{10}$, $SO_2R^{10}$, wherein $R^{10}$, $R^{11}$ and $R^{12}$ are as hereinbefore defined;

cyano, nitro, halogen, methylenedioxy, —$OR^{10}$, —$SR^{10}$, —$SOR^{10}$, —$SO_2R^{10}$, —$NHSO_2R^{10}$, —$SO_2NR^{11}R^{12}$, —$CO_2R^{10}$, $CONR^{11}$ $R^{12}$, $OCOR^{10}$, and —$NR^{11}$ $R^{12}$ where $R^{10}$, $R^{11}$ and $R^{12}$ are as defined above;

or a salt, ester or physiologically functional derivative thereof or a solvate of any thereof, with the provisos that:

(a) (I) $R^2$ and $R^3$ which may be the same or different, are each independently selected from —$COOR^{10}$ and —$C_{1-8}$alkyl substituted by one or more substituents selected from —$COR^{10}$, —$OCOR^{10}$, —$SR^{10}$, —$SOR^{10}$, —$SO_2R^{10}$ and $R^{10}$ is as hereinbefore defined, —$C_{3-7}$ cycloalkyl, nitro and aryl; or a salt, ester or physiologically functional derivative thereof or a solvate of any thereof; or (ii) $R^6$ and $R^7$, which may be the same or different, each represent one or more ring substituents selected from $CF_3$, cyano, —$CO_2R^{10}$, —$CONR^{11}$ $R^{12}$, —$SR^{10}$, —$SOR^{10}$, $SO_2R^{10}$, —$SO_2NR^{11}$ $R^{12}$ wherein $R^{10},R^{11}$ and $R^{12}$ are as hereinbefore defined, and $C_{1-6}$alkyl substituted by —$OR^{10}$ wherein $R^{10}$ is as hereinbefore defined; or a salt, ester or physiologically functional derivative thereof or a solvate of any thereof; or (iii) such compounds of formula (I), notwithstanding (I) and (ii) above, include the compounds 12,13-dihydro-2,10-difluoro-5-indolo[2,3-a]pyrrolo [3,4-c]carbazole-5,7-(6H)-dione and 12,13-dihydro-12-ethyl-5H-indolo]2,3-a]-pyrrolo[3,4-c]carbazole-5,7(6H)-dione; or a salt, ester or physiologically functional derivative thereof or a solvate thereof;

(b) such compounds of formula (I) do not include the compounds:

12,13-dihydro-6-phenyl-5H-indole[2,3-a]pyrrolo[3,4-c]carbazole-5,6(6H)-dione;

12,13-dihydro-1,11-bis(phenylmethoxy)-6-[(phenylmethoxy)-methyl]-5H-indolo[2,3-a]pyrrolo[3,4-c]carbazole-5,7(6H)-dione;

12,13-dihydro-6-methyl-5H-indolo[2,3-a]pyrrolo[3,4-a]carbazole-5,7(6H)-dione.

1,11-dichloro-12,13-dihydro-6-[(phenylmethoxy)methyl]-5H-indolo [2,3-a]pyrrolo[3,4-c]carbazole-5,7(6H)-dione; and 12,13-dihydro-6-(phenylmethyl)-5H-indolo[2,3-a]pyrrolo[3,4-c]carbazole-5,7( 6H)-dione.

8. A compound according to claim 8 wherein $R^1$ represents —$C_{1-8}$alkyl having one or more substituents selected from $C_{3-8}$cycloalkyl, —$OR^{10}$ where $R^{10}$ is H are aryl optionally substituted by one or more substituents selected from nitro and $C_{1-6}$alkyl wherein one or more hydrogen atoms are replaced by a halogen atom; or a salt, ester or physiologically functional derivative thereof.

9. A compound according to claim 8, wherein $R^1$ represents OH, cyclohexylmethyl, pyridylmethyl or phenylmethyl wherein the phenyl ring is substituted by one or more substituents selected from $CH_3$ and nitro; or cyclohexyl, $R^2$ and $R^3$, which may be the same or different, are each independently selected from H, t-butyloxycarbonyl, acetoxypropyl and ethyl; and $R^6$ and $R^7$, which may be the same or different, each represent one or more ring substituents selected from H, halogen and —$OR^{10}$ wherein $R^{10}$ is $C_{1-6}$alkyl; or a salt, ester or physiologically functional derivative thereof or a solvate of any thereof.

10. A compound according to claim 7 selected from:

12,13-Dihydro-6-(cyclohexylmethyl)-5H-indolo-[2,3a]pyrrolo-[3,4c]carbazole- 5,7(6H)-dione;

12,13-Dihydro-6-(3-trifluoromethylphenylmethyl)-5H-indolo-[2,3a]pyrrolo-[3,4c]carbazole-5,7(6H)-dione;

12,13-Dihydro-6(di-3,5-trifluoromethylphenylmethyl)-5H-indolo-[2,3a]pyrrolo-[3,4c]carbazole-5,7(6H)-dione;

12,13-Dihydro-6(2-pyridylmethyl)-5H-indolo-[2,3a]pyrrolo[3,4c]-carbazole- 5,7(6H)-dione;

12,13-Dihydro-6(3-nitrophenylmethyl)-5H-indolo-[2,3a]pyrrolo-[3,4c]-carbazole- 5,7(6H)-dione;

12,13-Dihydro-6(3-trifluoromethylphenylmethyl)-2,10-difluoro-5H-indolo-[2,3a]pyrrolo[3,4c]carbazole-5,7(6H)-dione;

12,13-Dihydro-2,10-difluoro-5H-indolo-[2,3a]pyrrolo[3,4c]carbazole- 5,7(6H)-dione;

12,13-Dihydro-6(3-trifluoromethylphenylmethyl)-12-(3-acetoxypropyl)-5H-indolo-[2,3a]pyrrolo[3,4c]carbazole-5,7(6H)-dione;

12,13-Dihydro-12-(tert-butyloxycarbonyl)-5H-indolo-[2,3a]pyrrolo-[3,4c]-carbazole- 5,7(6H)-dione; and 12,13-Dihydro-6-(hydroxy)-5H-indolo-[2,3a]pyrrolo[3,4c]carbazole- 5,7(6H)-dione;

or salts, esters and physiologically functional derivatives thereof and solvates of any thereof.

11. A pharmaceutical formulation comprising a compound according to claim 7 together with a pharmaceutically acceptable carrier therefore.

12. A formulation according to claim 7 in unit dosage form.

13. A formulation according to claim 7 in the form of a tablet or capsule.

* * * * *